United States Patent [19]

Saito et al.

[11] Patent Number: 5,084,468

[45] Date of Patent: Jan. 28, 1992

[54] DC-88A DERIVATIVES

[75] Inventors: Hiromitsu Saito, Sagamihara; Masaji Kasai, Fujisawa; Makoto Morimoto; Eiji Kobayashi, both of Shizuoka; Yoichi Uosaki, Machida, all of Japan; Yutaka Kanda, Houston, Tex.; Hiroshi Sano, Machida, Japan

[73] Assignee: Kyowa Hakko Kogyo Co., Ltd., Tokyo, Japan

[21] Appl. No.: 392,271

[22] Filed: Aug. 10, 1989

[30] Foreign Application Priority Data

Aug. 11, 1988 [JP] Japan ................... 63-200352
Oct. 21, 1988 [JP] Japan ................... 63-265581
Feb. 14, 1989 [JP] Japan ................... 1-34482

[51] Int. Cl.$^5$ .................. A61K 31/40; C07D 487/02
[52] U.S. Cl. .................. 514/367; 514/375; 514/394; 514/397; 514/411; 548/159; 548/217; 548/327; 548/336; 548/433
[58] Field of Search ........... 548/433, 217, 159, 327, 548/336; 514/411, 375, 367, 394, 397

[56] References Cited

U.S. PATENT DOCUMENTS

| 4,169,888 | 10/1979 | Hanka et al. ............. | 435/128 |
| 4,400,518 | 8/1983 | Wierenga ............. | 548/433 |
| 4,413,132 | 11/1983 | Wierenga ............. | 548/433 |
| 4,423,228 | 12/1983 | Wierenga ............. | 548/421 |
| 4,423,229 | 12/1983 | Wierenga ............. | 548/421 |
| 4,423,230 | 12/1983 | Wierenga ............. | 548/433 |

FOREIGN PATENT DOCUMENTS

| 154445 | 9/1985 | European Pat. Off. . |
| 318056 | 5/1989 | European Pat. Off. . |
| 0339681 | 11/1989 | European Pat. Off. . |
| 8706265 | 10/1987 | World Int. Prop. O. . |
| 8804659 | 6/1988 | World Int. Prop. O. . |

OTHER PUBLICATIONS

Warpehoski et al., J. Med. Chem., vol. 31 (1988), pp. 590-603.
Wierenga et al., Adv. Enzyme Regul., Antitumor Analogs of CC-1065, pp. 141-155.

Primary Examiner—Mary E. Ceperley

Attorney, Agent, or Firm—Fitzpatrick, Cella, Harper & Scinto

[57] ABSTRACT

A novel DC-88A derivative represented by general formula:

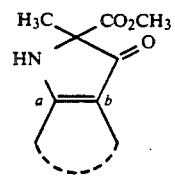

wherein

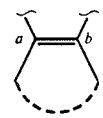

represents

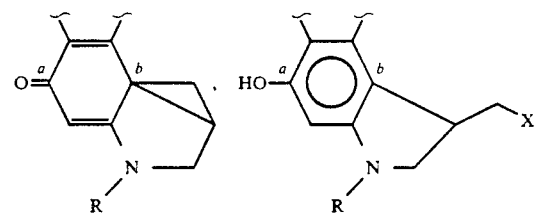

or 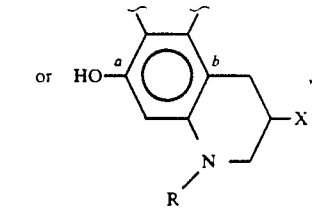

has an excellent antitumor activity and is useful as an antitumor agent.

10 Claims, No Drawings

DC-88A DERIVATIVES

BACKGROUND OF THE INVENTION

The present invention relates to novel DC-88A derivatives. The compound have an excellent antitumor activity and are useful as antitumor agents.

WO 87/06265 (EP-A-0271581) discloses DC-88A produced by microorganisms belonging to the genus Streptomyces exhibits not only an antibacterial activity against various bacteria but also an antitumor activity against lymphocytic leukemia P388, etc.

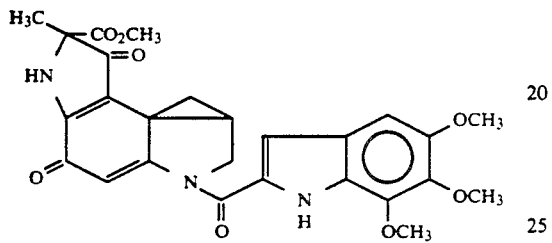

DC-89A1 which is a compound having a structure similar to DC-88A is disclosed in WO 87/06265; DC-89A2, DC-89B1 and DC-89B2 are disclosed in Japanese Patent Application No. 182866/88. DC-89A1, DC-89A2, DC-89B1 and DC-89B2 have the following structures.

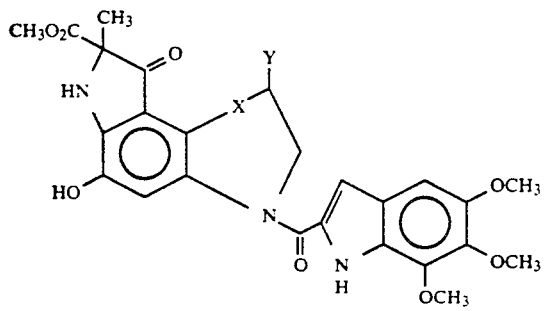

DC-89A1: X = —CH$_2$—, Y = Cl
DC-89A2: X = single bond, Y = —CH$_2$Cl
DC-89B1: X = —CH$_2$—, Y = Br
DC-89B2: X = single bond, Y = —CH$_2$Br These compounds show an antibacterial activity against various bacteria and an antitumor activity against lymphocytic leukemia P388, etc.

CC-1065 and its derivative which are structurally similar to DC-88A and exhibit an antitumor activity are also disclosed in Japanese Published Unexamined Patent Application Nos. 64695/79 and 193989/85.

DC-88A derivatives having an excellent antitumor activity have always been demanded.

SUMMARY OF THE INVENTION

The present invention provides novel DC-88A derivatives represented by general formula (A):

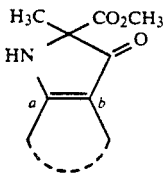  (A)

wherein

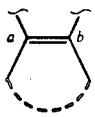

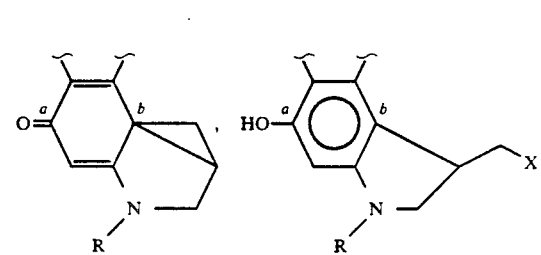

or 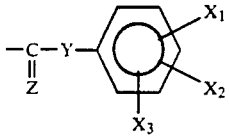, wherein X represents chlorine, bromine or iodine; R represents one member selected from hydrogen, and the groups (a), (b), (c), (d) and (e):

(a)

$$-\underset{Z}{\overset{\|}{C}}-Y-\underset{X_3}{\overset{X_1}{\bigcirc}}X_2$$

wherein each of $X_1$, $X_2$ and $X_3$ independently represents hydrogen, —OH, —CHO, —OR$_1$ (wherein R$_1$ represents a straight or branched alkyl having 1 to 7 carbon atoms or benzyl), —OCOR$_1$ (wherein R$_1$ has the same significance as described above), —NO$_2$, —NH$_2$, —NR$_2$R$_3$ (wherein each of R$_2$ and R$_3$ represents hydrogen or R$_1$, and R$_1$ has the same significance as described above), —NR$_2$COR$_1$ (wherein R$_1$ and R$_2$ have the same significances as described above), —NHCO$_2$R$_1$ (R$_1$ has the same significance as described above), —NHCONH$_2$, —SH, —SR$_1$ (wherein R$_1$ has the same significance as described above), —SCOR$_1$, (wherein R$_1$ has the same significance as described above), chlorine or bromine; or X$_1$ and X$_2$ are combined together to represent —OCH$_2$)—; Z represents O, S or NH; Y represents —CH$_2$—$_l$ (wherein l is an integer of 0 to 7), —CH=CH—$_m$ (wherein m is an integer of 1 or 2), —Y'— (wherein Y' represents O, S or NH), —Y'—(CH$_2$)$_n$—(wherein Y' has the same significance as described above and n represents an integer of 1 to 4), —(CH$_2$)$_n$—Y'— (wherein Y' and n have the same significance as described above) or

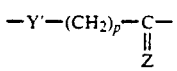

(wherein Y' and Z have the same significances as described above and p represents an integer of 0 to 4);

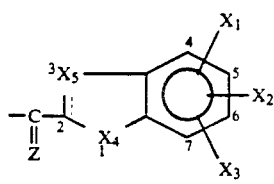

wherein $X_1$, $X_2$, $X_3$ and Z have the same significances as described above; $X_4$ represents O, S, NH or $NR_1$ (wherein $R_1$ has the same significance as described above); and $X_5$ represents —N=, —CH= or —$CH_2$—; provided that when X is Cl or Br and $X_1$, $X_2$ and $X_3$ are 5—$OCH_3$, 6—$OCH_3$ and 7—$OCH_3$, respectively and Z is O and $X_4$ is —NH—, $X_5$ is =N— or —$CH_2$—;

wherein $R_4$ represents a straight or branched alkyl having 1 to 7 carbon atoms or an alkyl wherein any one of the hydrogen atoms in the above alkyl is substituted with $X_1$; and $X_1$ has the same significance as described above;

(d) —$R_5$—$R_6$ wherein $R_5$ represents a substituent obtained by removing hydrogen from —$NH_2$ which is represented by $X_1$, $X_2$ or $X_3$ of the substituent group (a), (b) or (c); and $R_6$ represents the substituent group (a), (b) or (c) described above; or, (e) a residue obtained by removing hydroxy of the carboxylic acid in an α-amino acid, benzyloxycarbonyl group or tert-butoxycarbonyl group, and pharmaceutically acceptable salts thereof.

DETAILED DESCRIPTION OF THE INVENTION

The compounds represented by general formula (A) are hereinafter referred to as Compound (A).

Compounds represented by formulae with numbers I, II, III ... are similarly referred to as Compound I, II, III ....

Compound (II)-a and Compound (III)-a are included in Compound (II) and Compound (III), respectively.

In the definition of the groups (a) and (c) under the substituent R, a straight or branched alkyl having 1 to 7 carbon atoms includes, for example, methyl, ethyl, propyl, isopropyl, butyl, isobutyl, sec-butyl, tert-butyl, pentyl, neopentyl, hexyl, heptyl, etc.

In the definition of the group (e) under the substituent R, the α-amino acid includes, for example, glycine, alanine, leucine, glutamic acid, aspartic acid, lysine, serine, proline, phenylalanine, tyrosine, tryptophan and histidine.

Processes for producing Compound (A) are described below.

In general formula (A), Compound (IV) wherein

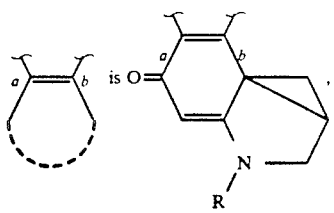

and R is hydrogen can be obtained by reacting DC-88A with a base.

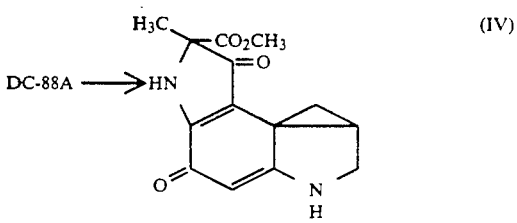

As the base, mention may be made of sodium methoxide, sodium hydroxide, potassium hydroxide, potassium t-butoxide, triethylamine, 1,8-diazabicycloundecene (DBU), potassium carbonate, etc. The base is used generally in 1 to 3 molar equivalents based on DC-88A. As an inert solvent, water, methanol, tetrahydrofuran (THF), dioxane, acetonitrile, etc are used singly or as admixture. The reaction is carried out generally at −20° to 50° C. and completed in 30 minutes to 5 hours. Purification is effected by column chromatography or high performance liquid chromatography (HPLC).

In general formula (A), Compound (I) wherein:

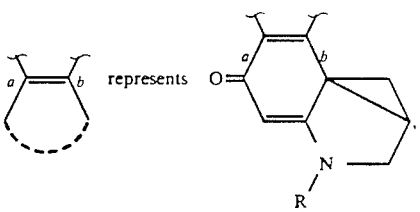

and R is the substituents other than hydrogen can be produced by the following step.

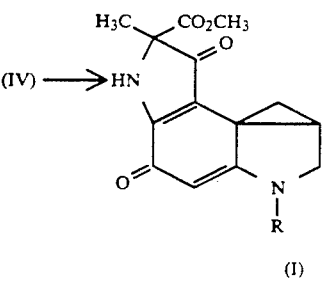

Compound (I) can be produced by reacting compound (IV) either with a carboxylic acid reactive derivative, or with isocyanate, isothiocyanate or benzyl chloroformate derivative in an inert solvent in the presence of a base.

Examples of the base include sodium hydride, lithium diisopropylamide, potassium t-butoxide, triethylamine, 4-dimethylaminopyridine, etc. The base is used in 1 to 2 molar equivalents based on Compound (IV). As the inert solvent, dimethylformamide, THF, toluene, dimethylsulfoxide, pyridine, etc. may be used singly or as admixture. Examples of the carboxylic acid reactive derivative include an acid chloride, an acid anhydride (an acid anhydride produced using N,N'-dicyclohexylcarbodiimide, etc.), an activated ester (p-nitrophenyl ester, N-hydroxysuccinimide ester, etc.), an activated amide (imidazolide, etc.), a mixed acid anhydride (mixed acid anhydride with monoethyl carbonate, monoisobutyl carbonate, etc.), etc. The reactive derivative is used generally in 1 to 2 molar equivalents based on Compound (IV). Isocyanate or isothiocyanate is used in 1 to 2 molar equivalents based on Compound (IV). The reaction is carried out generally at −50° to 30° C. and completed in 30 minutes to one day.

Among the carboxylic acid reactive derivative, isocyanate and isothiocyanate, those containing reactive functional groups therein should be protected upon acylation. The thus obtained protected compounds are acylated and the protective group is removed after the acylation. Selection and removal of protective groups are described in T. W. Greene, "Protective Groups in Organic Synthesis", John Wiley & Sons, 1980, in detail.

Processes for producing Compound (II0 of general formula (A) wherein:

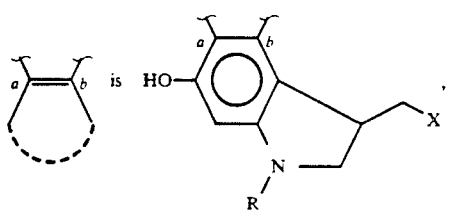

and Compound (III) wherein:

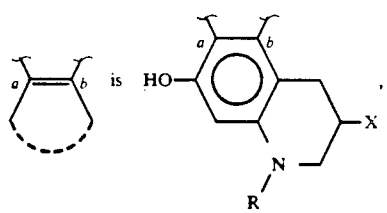

are described below.

Compound (II) and Compound (III) can be obtained by reacting Compound (I) with hydrochloric acid, hydrobromic acid or hydroiodic acid in an inert solvent.

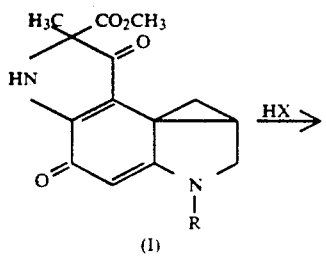

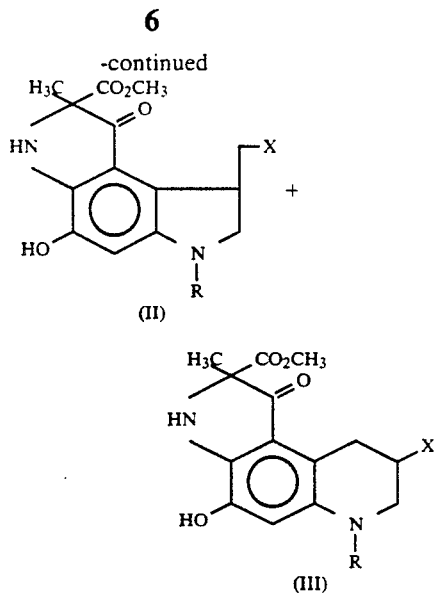

wherein X is Cl, Br or I. As the inert solvent, dimethylformamide, acetonitrile, methylene chloride, toluene, water, etc. may be used singly or as admixture. Hydrochloric acid (X=Cl), hydrobromic acid (X=Br) or hydroiodic acid (X=I) is used in 1 to 20 molar equivalents based on Compound (I). The reaction is carried out generally at −30° to 30° C. and completed in one minute to 5 hours.

Alternatively, Compound (II) and Compound (III) can also be obtained by reacting Compound (I) with a halide of alkali metal or alkaline earth metal in a mixture of an inert solvent and a buffer solution having a pH range of 4 to 6. As the inert solvent, dimethylformamide, acetonitrile, THF, dioxane, etc. may be used singly or as admixture. As the buffer solution having a pH range of 4 to 6, buffer solutions composed of potassium primary citrate-sodium hydroxide, sodium secondary citrate-sodium hydroxide, potassium primary phosphate-sodium secondary phosphate, etc. are used in a concentration of 0.05 to 0.5M. The halide of alkali metal or alkaline earth metal includes, for example LiCl, NaCl, KCl, MgCl₂, CaCl₂, LiBr, NaBr, KBr, MgBr₂, CaBr₂, LiI, NaI, KI, MgI₂, etc. and is used generally in 2 to 30 molar equivalents based on Compound (I). The reaction is carried out generally at 0° to 50° C. and completed in 2 minutes to 2 days.

Compound (II) and Compound (III) can also be obtained by the following process. That is, in Compound (II)-a and Compound (III)-a containing benzyloxycarbonyl group or t-butoxycarbonyl group in R which can be readily splittable, R is removed to produce Compound (V) and Compound (VI), respectively.

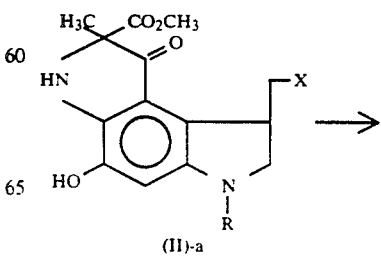

-continued

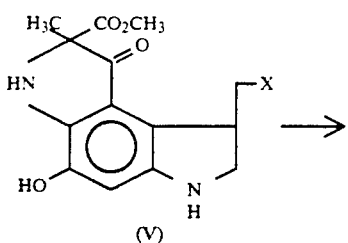
(V)

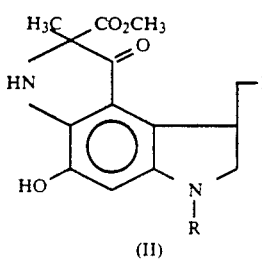
(II)

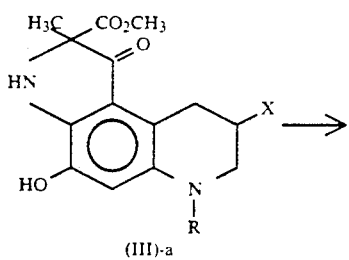
(III)-a

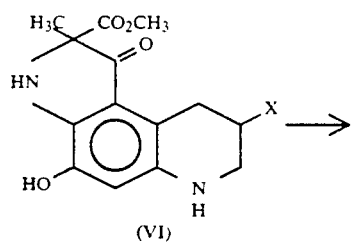
(VI)

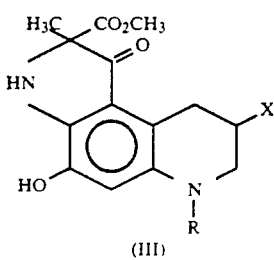
(III)

In the case of Compound (II)-a wherein R is benzyloxycarbonyl group, it is appropriate to remove R by hydrogenolysis in a conventional manner; removal with HBr-CH₃COOH is also applicable. In the case of Compound (III)-a wherein R is t-butoxycarbonyl group, R is removed with trifluoroacetic acid. Substituent R is introduced into Compound (V) and Compound (VI) by reacting Compound (V) and Compound (VI) with one of a carboxylic acid reactive derivative, isocyanate, isothiocyanate, etc. in an inert solvent, if necessary, in the presence of a base.

As the inert solvent, dimethylformamide, THF, toluene, methylene chloride, chloroform, pyridine, etc. may be used singly or as admixture. Examples of the carboxylic acid reactive derivative include an acid chloride, an acid anhydride, an activated ester (p-nitrophenyl ester, N-hydroxysuccinimide ester, etc.), an activated amide (imidazolide, etc.), a mixed acid anhydride (mixed acid anhydride with monoethyl carbonate, monoisobutyl carbonate, etc.). The reactive derivative, isocyanate or isothiocyanate is used generally in 1 to 2 molar equivalents based on Compound (V) or Compound (VI). The reaction is carried out generally at −20° to 50° C. and completed in 30 minutes to one day. Alternatively, the carboxylic acid and a condensing agent are simultaneously reacted with Compound (V) or Compound (VI) in an inert solvent to produce Compound (II) or Compound (III). As the condensing agent, dicyclohexylcarbodiimide or similar carbodiimides are appropriate. The condensing agent and the carboxylic acid are both employed in 1 to 2 molar equivalents based on Compound (V) or Compound (VI). As the inert solvent, acetonitrile, methylene chloride, THF, dimethylformamide, etc. may be used. The reaction is carried out generally at −20° to 50° C. and completed in 30 minutes to one day.

After completion of the reaction in each step, a buffer solution is added to the reaction mixture, if necessary, followed by extracting with a non-aqueous solvent such as ethyl acetate, chloroform, ether, etc. After washing with water, a sodium chloride aqueous solution, etc., the extract is dried over anhydrous sodium sulfate and the solvent is distilled off. The residue obtained is subjected to silica gel column chromatography, thin layer chromatography, high performance liquid chromatography, recrystallization, etc. to effect purification.

The structure and compound number of representative compounds which fall under Compound (I), Compound (II) and Compound (III) are shown in Table 1. In Table 1, types (I), (II) and (III) indicate that they fall under Compound (I), Compound (II) and Compound (III), respectively.

TABLE 1
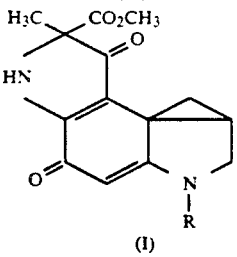
(I)
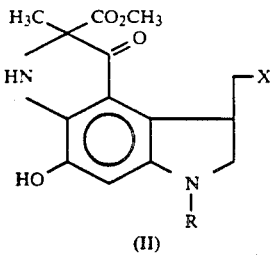
(II)
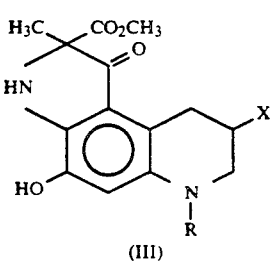
(III)
| Compound No. | Type | R | X |
|---|---|---|---|
| 1 | (I) | 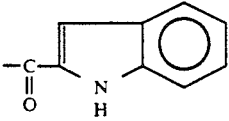 | — |
| 2 | (II) | 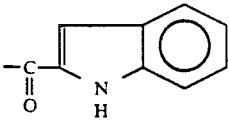 | Br |
| 3 | (II) | 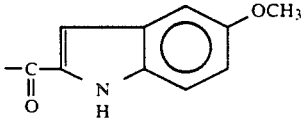 | Br |
| 4 | (II) | 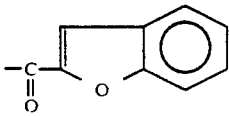 | Br |
| 5 | (II) | 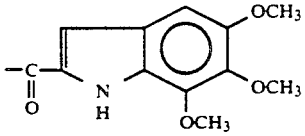 | I |
| 6 | (I) | 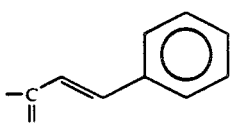 | — |
| 7 | (II) | 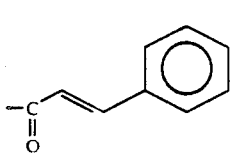 | Br |

TABLE 1-continued
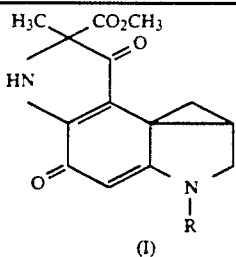
(I)
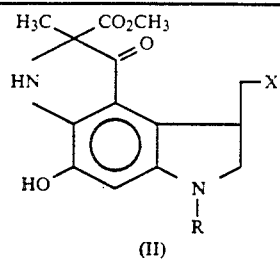
(II)
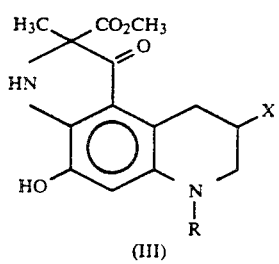
(III)
| Compound No. | Type | R | X |
|---|---|---|---|
| 8 | (I) | —C(=O)—NH—Ph | — |
| 9 | (II) | —C(=O)—NH—Ph | Br |
| 10 | (I) | —C(=O)—Ph | — |
| 11 | (II) | —C(=O)—Ph | Br |
| 12 | (I) | —C(=O)—NHCH₂—Ph | — |
| 13 | (II) | —C(=S)—NHCH₂—Ph | Br |
| 14 | (I) | —C(=O)—CH₂O—Ph | — |
| 15 | (II) | —C(=O)—CH₂O—Ph | Br |
| 16 | (I) | —C(=O)—OCH₂—Ph | — |

TABLE 1-continued
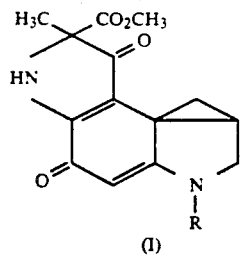
(I)
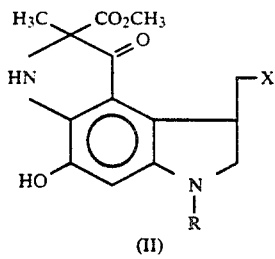
(II)
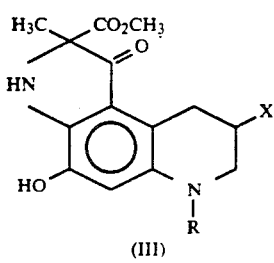
(III)
| Compound No. | Type | R | X |
|---|---|---|---|
| 17 | (I) | —C(=O)—NHCO—C₆H₅ | — |
| 18 | (I) | H | — |
| 19 | (II) | —C(=O)—CH₂NH—C₆H₅·HBr | Br |
| 20 | (II) | —C(=O)—NHCO—C₆H₅ | Br |
| 21 | (I) | —C(=O)—CH₃ | — |
| 22 | (II) | —C(=O)—CH₃ | Br |
| 23 | (I) | —C(=O)— 5,6-dimethoxyindol-2-yl | — |
| 24 | (II) | —C(=O)— 5,6-dimethoxyindol-2-yl | Br |
| 25 | (I) | —C(=O)— benzothiophen-2-yl | — |

TABLE 1-continued
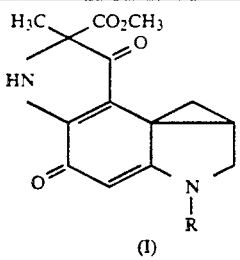
(I)
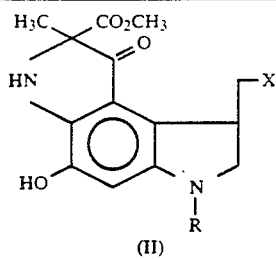
(II)
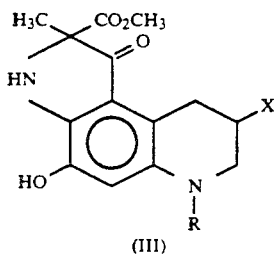
(III)
| Compound No. | Type | R | X |
|---|---|---|---|
| 26 | (II) | ![benzothiophene-2-carbonyl] -C(=O)-(benzo[b]thiophen-2-yl) | Br |
| 27 | (I) | -C(=O)-CH=CH-(3-methoxyphenyl) | — |
| 28 | (II) | -C(=O)-CH=CH-(3-methoxyphenyl) | Br |
| 29 | (I) | -C(=O)-CH=CH-(3,4-dimethoxyphenyl) | — |
| 30 | (II) | -C(=O)-CH=CH-(3,4-dimethoxyphenyl) | Br |
| 31 | (II) | -C(=O)-(indolin-2-yl)·HBr | Br |
| 32 | (I) | -C(=O)-(5-(NHCO$_2$C(CH$_3$)$_3$)-1H-indol-2-yl) | — |

TABLE 1-continued
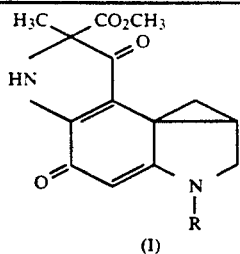
(I)
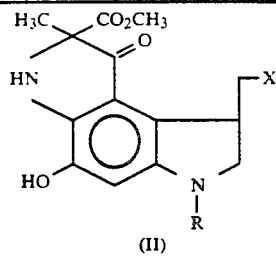
(II)
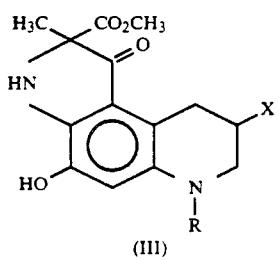
(III)
| Compound No. | Type | R | X |
|---|---|---|---|
| 33 | (II) | 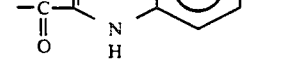 | Br |
| 34 | (II) | 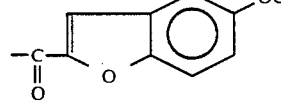 | Br |
| 35 | (II) |  | Br |
| 36 | (II) | 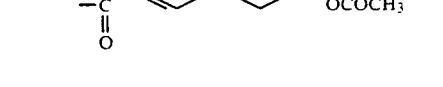 | Br |
| 37 | (II) | 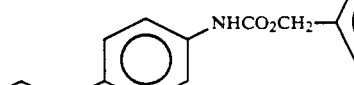 | Br |
| 38 | (II) |  | Br |
| 39 | (II) | 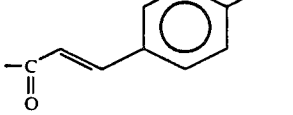 | Br |

TABLE 1-continued

Structures (I), (II), (III) shown.

| Compound No. | Type | R | X |
|---|---|---|---|
| 40 | (II) | –C(=O)–CH=CH–C6H4–N(CH3)2 (para) | Br |
| 41 | (II) | –C(=O)–CH=CH–C6H4–NO2 (para) | Br |
| 42 | (II) | –C(=O)–CH=CH–C6H4–CHO (para) | Br |
| 43 | (II) | –C(=O)–CH=CH–C6H2(OCH3)3 (3,4,5-trimethoxy) | Br |
| 44 | (II) | –C(=O)–CH=CH–C6H4–Cl (para) | Br |
| 45 | (II) | –C(=O)–(1H-indol-2-yl)-5-[(1H-indol-2-ylcarbonyl)amino] | Br |

TABLE 1-continued
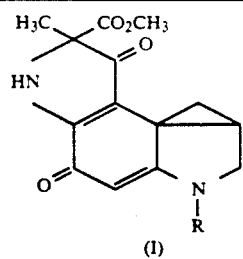
(I)
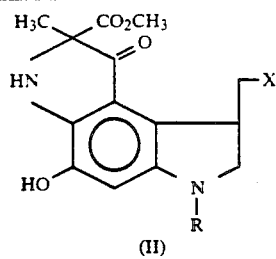
(II)
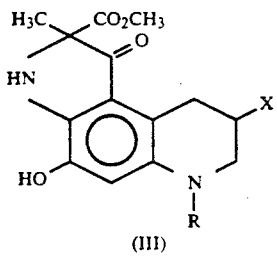
(III)
| Compound No. | Type | R | X |
|---|---|---|---|
| 46 | (II) | 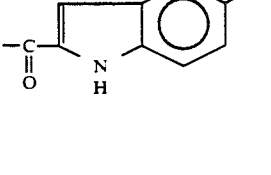 | Br |
| 47 | (II) | 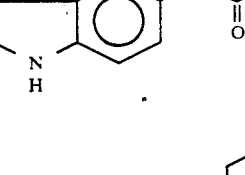 | Br |
| 48 | (II) | 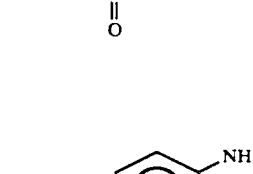 | Br |
| 49 | (II) | 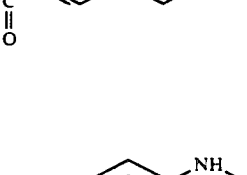 | Br |
| 50 | (II) | 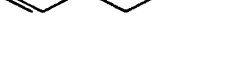 | Br |

TABLE 1-continued
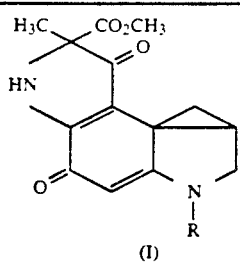
(I)
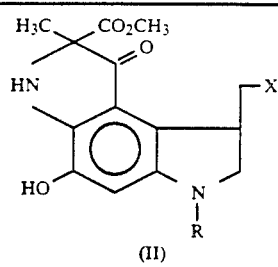
(II)
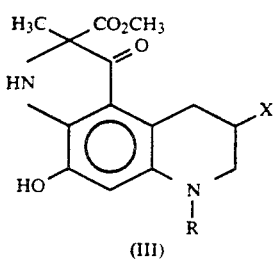
(III)
| Compound No. | Type | R | X |
|---|---|---|---|
| 51 | (I) | ![structure: cinnamoyl-phenyl-NHC(O)-indole] | — |
| 52 | (I) | ![structure: benzofuran-2-carbonyl with 5-NHC(O)-indole] | — |
| 53 | (I) | ![structure: methylenedioxyphenyl propenone] | — |
| 54 | (I) | ![structure: acetyl-pyrrole with trimethoxy/benzyloxy phenyl] | — |
| 55 | (II) | ![structure: acetyl-pyrrole with trimethoxy/benzyloxy phenyl] | Br |
| 56 | (I) | ![structure: CH₃C(O)CH₂O-C₆H₄-OCH₃] | — |

TABLE 1-continued

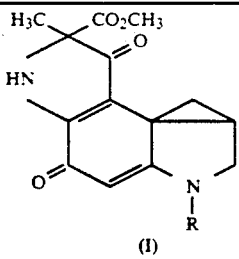
(I)

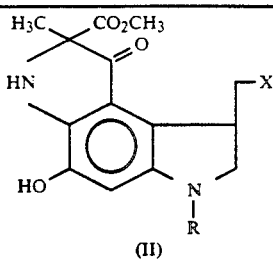
(II)

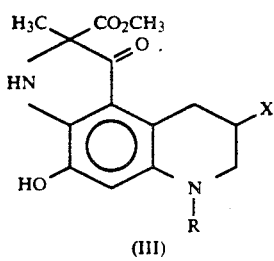
(III)

| Compound No. | Type | R | X |
|---|---|---|---|
| 57 | (I) | 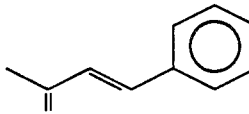 (4-NHCO$_2$C(CH$_3$)$_3$ phenyl-CH=CH-CH$_2$-C(=O)-) | — |
| 58 | (I) | 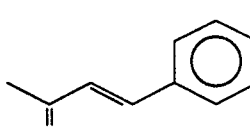 (4-NHCO$_2$CH$_3$ phenyl-CH=CH-CH$_2$-C(=O)-) | — |
| 59 | (I) | 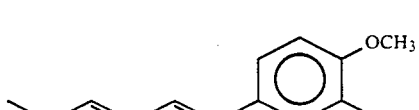 (3,4-dimethoxyphenyl-CH=CH-CH=CH-C(=O)-) | — |
| 60 | (I) |  (phenyl-CH=CH-CH=CH-C(=O)-) | — |
| 61 | (I) | 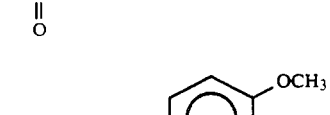 (4-OCH$_3$-3-NO$_2$ phenyl-CH=CH-CH$_2$-C(=O)-) | — |

Test on Growth Inhibition of HeLa S$_3$ cells

HeLa S$_3$ cells diluted to 3 x 10$^4$ cells/ml with MEM medium containing 10% calf fetal serum and 2 mM glutamine were separately distributed by 0.1 ml each in each well of a 96 well microtiter plate.

After culturing at 37° C. overnight in a CO$_2$-incubator, 0.05 ml each of a test sample appropriately diluted with MEM medium was added to each well.

After culturing the cells for 72 hours in the CO$_2$-incubator, the culture supernatant was removed. After washing once with phosphate buffered physiological saline (PBS), 0.1 ml each of MEM medium containing 0.02% neutral red was added to each well and then cultured at 37° C. for an hour in the CO$_2$-incubator to stain the cells. After removing the culture supernatant, the cells were washed once with physiological saline, and the dye was extracted with 0.001N HCl/30% ethanol. Absorbance at 550 mm of the extract was measured with a microplate reader. By comparing absorbance of extract of intact cells with that of the cells treated with a test compound in known concentrations, IC$_{50}$, i.e. a drug concentration which inhibited growth of the cells by 50% was determined.

$IC_{50}$ values of representative Compound (I), Compound (II) and Compound (III) are shown in Table 2.

TABLE 2

| Compound No. | $IC_{50}$ (nM) |
| --- | --- |
| 1 | 1.1 |
| 2 | 0.054 |
| 3 | 0.0034 |
| 4 | 0.10 |
| 5 | 0.011 |
| 6 | 2.3 |
| 7 | 5.7 |
| 8 | 3.2 |
| 9 | 2.6 |
| 14 | 6.7 |
| 15 | 3.1 |
| 18 | 3900 |
| 23 | <0.024 |
| 24 | 0.024 |
| 25 | 7.6 |
| 27 | 0.60 |
| 28 | 2.5 |
| 29 | <0.024 |
| 30 | 0.034 |
| 31 | 81 |
| 32 | 0.0075 |
| 33 | 0.88 |
| 34 | 0.050 |
| 35 | 0.94 |
| 37 | 0.74 |
| 38 | 0.035 |
| 40 | 0.085 |
| 45 | 1.1 |
| 46 | 0.4 |
| 48 | 1.2 |
| 55 | 0.52 |

Acute Toxity Test

Using dd strain male mice weighing 20±1 g, a test compound was intraperitoneally administered. MLD (the minimum lethal dose) was determined by observing the mortality for 14 days after administration.

The results are shown in Table 3.

TABLE 3

| Compound No. | Acute Toxicity (MLD) mg/kg |
| --- | --- |
| 2 | 0.25 |
| 3 | 0.063 |
| 4 | 0.25 |
| 7 | 1.0 |
| 15 | 4.0 |
| 19 | 2.5 |
| 22 | 13 |
| 24 | 0.25 |
| 26 | 2.2 |
| 28 | 0.16 |
| 30 | 0.082 |
| 31 | 20 |
| 32 | 0.25 |
| 34 | 0.063 |
| 35 | 0.25 |
| 36 | 1.3 |
| 38 | 0.063 |
| 39 | 1.3 |
| 40 | 0.31 |
| 41 | 1.3 |
| 42 | 2.5 |
| 45 | 0.63 |
| 46 | 0.63 |
| 55 | 0.25 |

Compound (A) may be used as antitumor agents singly or together with pharmacologically acceptable carriers. For example, Compound (A) is dissolved in a physiological saline solution or in an aqueous solution of glucose, lactose, mannitol, etc. to prepare a suitable pharmaceutical composition for injection. Alternatively, Compound (A) or salt thereof is freeze-dried or mixed with sodium chloride to prepare a powdery injection. The pharmaceutical composition may contain additives well known in the art of medical preparation, for example, pharmacologically acceptable salts, etc., if necessary. Although the amount of the compound for dosage varies depending upon age, condition, etc. of the patient, it is suitable to administer the compound in an amount of 0.0001 to 5 mg/kg/day for mammals including human beings. Administration is made once a day (single administration or consecutive administration) or intermittently 1 to 3 times a week or once 2 to 3 weeks, intravenously. If it is wished, oral administration is also possible in a similar dose and in a similar manner. Form of oral administration includes a tablet, a capsule, powders, granules, an ampoule, etc. These preparations contain pharmaceutical aids well known in the art of medical preparation. If it is wished, intraarterial administration, intraperitoneal administration, intrathoracic administration, etc. may also be possible in a similar dose and in a similar route.

The antitumor composition of this invention is expected to be effective for leukemia, gastric cancer, colon cancer, lung cancer, breast cancer, uterine cancer, etc. in mammals including human beings.

Certain specific embodiments of the present invention are illustrated by the following examples and reference examples.

Physicochemical properties of the compounds shown in the following examples and reference examples were determined with the following equipments.

| NMR | JEOL, Ltd. | FX-100 (100 MHz) |
| --- | --- | --- |
|  | JEOL, Ltd. | PS-100 (100 MHz) |
|  | Bruker | AM-400 (400 MHz) |
| MS | Hitachi Ltd. | M-80B |
|  | Shimadzu | QP-1000 |
| IR | Nippon Bunko | IR-810 |

As silica gel, Wakogel C-200® manufactured by WAKO Pure Chemical Industry Co., Ltd. was used.

In the following examples and reference examples, "treated in a conventional manner" refers to the following working-up reaction.

Citrate or phosphate buffer of pH 5 is added to the reaction mixture and the mixture is extracted with ethyl acetate or chloroform. The extract is washed with saturated aqueous sodium chloride solution. After drying over anhydrous sodium sulfate, the solvent is distilled off.

EXAMPLE 1: SYNTHESIS OF COMPOUND 18

DC-88A, 93 mg (0.18 mmol), was dissolved in 10 ml of methanol and 70 µl of methanolic solution containing 28% sodium methoxide was dropwise added to the solution under ice cooling. The mixture was stirred for 40 minutes under ice cooling, 0.1M phosphate buffer (pH 5.3) was added to the mixture, and methanol was distilled off. After adding sodium chloride to the residue, the mixture was extracted 3 times with ethyl acetate-THF. After drying over anhydrous sodium sulfate, the extract was concentrated under reduced pressure. The residue was purified by silica gel column chromatography [12 ml of silica gel, eluting solvent: chloroform: acetone = 1:0–3:1] to give 49 mg of Compound 18 (yield: 97%).

Physicochemical properties of Compound 18 are as follows.

$^1$H-NMR(CDCl$_3$) δ(ppm); 6.16 (br s 1H), 5.74 (s, 1H), 5.46 (br s 1H), 3.81 (ddd 1H J=11.0, 5.6, 1.5 Hz), 3.73 (s 3H), 3.69 (d 1H J=11.0 Hz), 3.03 (m 1H), 2.05 (dd 1H J=7.8, 3.5 Hz), 1.63 (s 3H), 1.01 (dd 1H J=4.6, 3.5 Hz).

IR (CHCl$_3$) γ$_{max}$(sm$^{-1}$): 3450, 1740, 1685, 1560.

SI-MS m/z: 275 (M+1)$^+$.

EXAMPLE 2: SYNTHESIS OF COMPOUND 1

In an argon atmosphere, 11.0 mg (0.26 mmol) of 60% sodium hydride was suspended in 1.0 ml of dimethylformamide and 0.7 ml of a dimethylformamide solution containing 60 mg (0.22 mmol) of Compound 18 was dropwise added to the solution at −15° to −10° C. Then the mixture was stirred at −15° to −3° C. for 20 minutes. After cooling to −30° C., 0.7 ml of a dimethyl formamide solution containing 50 mg (0.26 mmol) of indole-2-carbonyl chloride was dropwise added to the reaction mixture. The mixture was stirred at −30° to −5° C. for 50 minutes. The reaction mixture was treated in the conventional manner to give 113 mg of crude product. The crude product was purified by silica gel column chromatography (15 ml of silica gel, eluting solvent; chloroform: acetone=1:0–50:1) to give 68.9 mg of Compound 1 (yield; 75.5%).

Physicochemical properties of Compound 1 are as follows.

$^1$H-NMR(DMSO-d$_6$) δ(ppm); 11.83 (s 1H), 8.71 (s 1H), 7.68 (d 1H J=8.1 Hz), 7.48 (dd 1H J=8.3, 0.8 Hz), 7.28 (ddd 1H J=8.2, 7.0, 1.2 Hz), 7.21 (d 1H J=1.3 Hz), 7.09 (ddd 1H J=8.0, 7.0, 1.0 Hz), 6.94 (s 1H), 4.59 (dd 1H J=10.5, 5.3 Hz), 4.45 (d 1H J=10.5 Hz), 3.61 (s 3H), 3.02 (m 1H), 1.95 (dd 1H J=7.5, 3.5 Hz), 1.46 (s 3H), 1.45 (M 1H).

SI-MS m/z; 418(M+1)$^+$, 419(M+2)$^+$, 420(M+3)$^+$, 276, 275, 217, 215.

IR(KBr) γ$_{max}$(cm$^{-1}$); 3350(br), 1732, 1651, 1621.

EXAMPLE 3: SYNTHESIS OF COMPOUND 2

Compound 1, 45 mg, was dissolved in 8 ml of methylene chloride and 40 μl of 48% hydrogen bromide aqueous solution was added to the solution. The mixture was stirred at room temperature for 25 minutes. The reaction mixture was treated in a conventional manner to give 65 mg of the crude product. The crude product was purified by silica gel column chromatography (10 ml of silica gel, eluting solvent; chloroform: acetone=1:0–50:1) to give 47.6 mg of Compound 2 (yield; 88.6%).

Physicochemical properties of Compound 2 are as follows.

$^1$H-NMR-(CDCl$_3$-CD$_3$OD) δ(ppm); 8.02 (br s 1H), 7.73 (dt 1H J=8.0, 0.9 Hz), 7.50 (dd 1H J=8.3, 0.9 Hz), 7.32 (ddd 1H J=8.3, 7.0, 1.0 Hz), 7.16 (ddd 1H J=8.0, 7.0, 1.0 Hz), 7.09 (d 1H J=0.8 Hz), 4.67 (dd 1H J=11.0, 9.3 Hz), 4.57 (dd 1H J=11.0, 4.1 Hz), 4.15 (m 1H), 3.99 (dd 1H J=10.1, 3.2 Hz), 3.76 (s 3H), 3.64 (dd 1H J=10.1, 8.3 Hz), 1.67 (s 3H).

SI-MS m/z; 498, 500 (M+1)$^+$.

IR(KBr) γ$_{max}$(cm$^{-1}$); 3390, 3320, 1717, 1686, 1609, 1510.

EXAMPLE 4: SYNTHESIS OF COMPOUND 3

In an argon atmosphere, 7.0 mg (0.175 mmol) of 60% sodium hydride was suspended in 0.6 ml of dimethylformamide and 0.7 ml of a dimethyl formamide solution containing 40 mg (0.146 mmol) of Compound 18 was dropwise added to the solution at −10° C. Then the mixture was stirred at −15° to −5° C. for 50 minutes and 0.8 ml of a dimethylformamide solution containing 50 mg (0.161 mmol) of p-nitrophenyl 5-methoxyindole-2-carboxylate was dropwise added to the reaction mixture at −20° C. After stirring at −20° to −10° C. for 2 hours, the reaction mixture was treated in a conventional manner to give 91 mg of the crude product. The crude product was dissolved in 5 ml of methylene chloride and 40 μl of 48% hydrogen bromide aqueous solution was added to the solution followed by stirring at room temperature for 25 minutes. The reaction mixture was treated in the conventional manner to give the crude product. The crude product was purified by silica gel column chromatography (10 ml of silica gel, eluting solvent; chloroform: acetone=1:0–30:1) to give 24.7 mg of Compound 3 (yield; 32.0%).

Physicochemical properties of Compound 3 are as follows.

$^1$H-NMR(CDCl$_3$-CD$_3$OD) δ(ppm); 7.99 (br s 1H), 7.36 (d 1H J=8.9 Hz), 7.12 (d 1H J=2.3 Hz), 7.01 (dd 1H J=8.9, 2.3 Hz), 7.00 (d 1H J=0.6 Hz), 4.63 (dd 1H J=10.9, 9.3 Hz), 4.55 (dd 1H J=10.9, 4.3 Hz), 4.16 (m 1H), 4.03 (dd 1H J=10.0, 3.3 Hz), 3.87 (s 3H), 3.77 (s 3H), 3.59 (dd 1H J=10.0, 8.7 Hz), 1.69 (s 3H)

SI-MS m/z; 528, 530(M+1)$^+$.

IR(KBr) γ$_{max}$(cm$^{-1}$); 3350(br), 1733, 1696, 1684, 1623, 1505.

EXAMPLE 5: SYNTHESIS OF COMPOUND 4

In an argon atmosphere, 7.0 mg (0.175 mmol) of 60% sodium hydride was suspended in 0.6 ml of dimethylformamide and 0.7 ml of a dimethylformamide solution containing 40 mg of Compound 18 was dropwise added to the solution at −20° to −10° C. After the mixture was stirred at −20° to −10° C. for one hour and 10 minutes, 0.8 ml of a dimethylformamide solution containing 45 mg of p-nitrophenyl benzofuran-2-carboxylate was dropwise added to the reaction mixture at −20° C. After stirring at −20° to −10° C. for 40 minutes, the reaction mixture was treated in the conventional manner. The obtained residue (82 mg) was dissolved in 14 ml of acetonitrile and 40 μl of 48% hydrogen bromide aqueous solution was added to the solution followed by stirring at room temperature for 25 minutes. The reaction mixture was treated in the conventional manner to give 88 mg of the residue. The residue was purified by silica gel column chromatography (10 ml of silica gel, eluting solvent; n-hexane: ethyl acetate=2:1) to give 40.8 mg of Compound 4 (yield; 53.2%).

Physicochemical properties of Compound 4 are as follows.

$^1$H-NMR(CDCl$_3$) δ(ppm); 10.43 (br 1H), 8.56 (s 1H), 7.77 (m 1H), 7.70 (d 1H J=0.9 Hz), 7.63 (dd 1H J=8.4, 0.8 Hz), 7.49 (ddd 1H J=8.4, 7.2, 1.2 Hz), 7.37 (ddd 1H J=8.0, 7.2, 0.8 Hz), 4.75 (dd 1H J=11.9, 9.1 Hz), 4.68 (dd 1H J=11.9, 4.4 hz), 4.16 (m 1H), 4.01 (dd 1H J=10.1, 3.2 Hz), 3.79 (s 3H), 3.66 (dd 1H J=10.1, 8.3 Hz), 1.72(s 3H).

SI-MS m/z; 499, 501 (M+1)$^+$.

IR(KBr) γ$_{max}$(cm$^{-1}$); 3360(br), 1740, 1702, 1696, 1602, 1508.

EXAMPLE 6: SYNTHESIS OF COMPOUND 5

DC-88A, 40 mg (0.079 mmol), was dissolved in 8 ml of acetonitrile and 40 μl of 57% hydrogen iodide aqueous solution was added to the solution followed by stirring at room temperature for 15 minutes. The reaction mixture was treated in the conventional manner to give 48 mg of the crude product. The crude product was purified by silica gel column chromatography (10 ml of silica gel; eluting solvent; chloroform: acetone=1:0-30:1 ) to give 41.8 mg of Compound 5 (yield; 83.5%).

Physicochemical properties of Compound 5 are as follows.

$^1$H-NMR(CDCl$_3$) δ(ppm); 9.57 (br 1H), 9.52 (br s 1H), 8.49 (s 1H), 7.01 (d 1H J=2.3 Hz), 6.88 (s 1H), 4.62 (dd 1H J=10.9, 9.4 Hz), 4.39 (dd 1H J=10.9, 4.4 Hz), 4.15 (s 3H), 4.06 (m 1H), 3.96 (s 3H), 3.92 (s 3H), 3.84 (dd 1H J=9.9, 3.1 Hz), 3.74 (s 3H), 3.48 (dd 1H J=9.9, 8.7 Hz), 1.70 (s 3H).

SI-MS m/z; 636 (M+1)$^+$, 510, 402.

IR(KBr) $\gamma_{max}$(cm$^{-1}$); 3350(br), 1740, 1690, 1612, 1502.

EXAMPLE 7: SYNTHESIS OF COMPOUND 6

In an argon atmosphere, 7.0 mg (0.175 mmol) of 60% sodium hydride was suspended in 0.6 ml of dimethylformamide and 0.7 ml of a dimethylformamide solution containing 40 mg (0.146 mmol) of Compound 18 was dropwise added to the solution at −20° C. After stirring at −20° to −10° C. for 30 minutes, 0.8 ml of a dimethylformamide solution of 35 mg (0.175 mmol) of N-trans-cinnamoylimidazole was dropwise added to the reaction mixture at −30° C. After stirring at −30° to −20° C. for 50 minutes, the reaction mixture was treated in the conventional manner to give 58 mg of the crude product. The crude product was purified by silica gel column chromatography (10 ml of silica gel; eluting solvent; chloroform: acetone=1:0-50:1) to give 46.1 mg of Compound 6 (yield; 78.2%).

Physicochemical properties of Compound 6 are as follows.

$^1$H-NMR(CDCl$_3$) δ(ppm); 7.84 (d 1H J=15.4 Hz), 7.54-7.57 (m 2H), 7.40-7.45 (m 3H), 6.87 (br 1H), 6.78 (d 1H) J=15.4 Hz), 6.01 (br s 1H), 4.24 (d 1H J=11.0 Hz), 4.18 (dd 1H J=11.0, 4.9 Hz), 3.75 (s 3H), 2.99 (m 1H), 2.27 (dd 1H J=7.7, 3.9 Hz), 1.66 (s 3H), 1.23 (dd 1H J=4.9, 4.0 Hz).

SI-MS m/z; 405(M+1)$^+$; 406(M+2)$^+$, 407(M+3)$^3$.

IR(KBr) $\gamma_{max}$ (cm$^{-1}$); 3300 (br), 1740, 1671, 1614, 1558.

EXAMPLE 8: SYNTHESIS OF COMPOUND 7

Compound 6, 33 mg, was dissolved in 4 ml of acetonitrile and 25 μl of 48% hydrogen bromide aqueous solution was added to the solution followed by stirring at room temperature for 15 minutes. The reaction mixture was treated in the conventional manner. The resulting crude product was purified by silica gel column chromatography (8 ml of silica gel, eluting solvent; chloroform: acetone=1:0-50:1) to give 25.3 mg of Compound 7 (yield; 63.9%).

Physicochemical properties of Compound 7 are as follows.

$^1$H-NMR(CDCl$_3$) δ(ppm); 8.06 (s 1H), 7.76 (d 1H J=15.4 Hz), 7.60-7.62 (m 2H), 7.41-7.46 (m 3H), 6.87 (d 1H J=15.4 Hz), 4.42 (dd 1H J=10.8, 9.8 Hz), 4.31(dd 1H J=10.8, 4.3 Hz), 4.13 (m 1H), 4.01 (dd 1H J=10.0, 3.2 hz), 3.76 (s 3H), 3.59 (dd 1H J=10.0, 8.7 Hz), 1.67 (s 3H).

IR(KBr) $\gamma_{max}$ (cm$^{-1}$); 1738, 1698, 1643, 1577, 1500.

EI-MS m/z; 486, 484(M$^+$), 404, 345, 274, 215.

EXAMPLE 9: SYNTHESIS OF COMPOUND 8

In an argon atmosphere, 7.0 mg (0.175 mmol) of 60% sodium hydride was suspended in 0.6 ml of dimethylformamide and 0.7 ml of a dimethylformamide solution containing 40 mg (0.146 mmol) of Compound 18 was dropwise added to the suspension at −20° C. After stirring at −20° to −10° C. for 2 hours, 0.7 ml of a dimethylformamide solution containing 19 μl 0 (0.175 mmol) of phenyl isocyanate was dropwise added to the reaction mixture at −30° C. After stirring at −30° to −20° C. for 45 minutes, the reaction mixture was treated in the conventional manner. The resulting crude product was purified by silica gel column chromatography (10 ml of silica gel, eluting solvent; chloroform: acetone=1:0-20:1) to give 12.6 mg of Compound 8 (yield; 22.0%).

Physicochemical properties of Compound 8 are as follows.

$^1$H-NMR(CDCl$_3$) δ(ppm); 7.40-7.43 (m 2H), 7.32-7.37 (m 2H) 7.15 (m 1H), 6.93 (br s 1H), 6.74 (s 1H) 6.03 (br s 1H), 4.17 (dd 1H J=10.6, 5.2 Hz), 4.04 (d 1H J=10.6 Hz), 3.75 (s 3H), 3.00 (ddd 1H J=7.7, 5.0, 5.0 Hz), 2.22 (dd 1H J=7.7, 3.9 Hz), 1.65 (s 3H), 1.21 (dd 1H J=4.9, 4.0 Hz).

SI-MS m/z; 394(M+1)$^+$, 395(M+2)$^+$, 396(M+3)$^+$.

IR(KBr) $\gamma_{max}$ (cm$^{-1}$); 1734, 1670, 1530, 1442.

EXAMPLE 10: SYNTHESIS OF COMPOUND 9

In an argon atmosphere, 6.4 mg (0.161 mmol) of 60% sodium hydride was suspended in 0.6 ml of dimethylformamide and 0.7 ml of a dimethylformamide solution containing 40 mg (0.146 mmol) of Compound 18 was dropwise added to the suspension at −20° C. After stirring at −20° to −10° C. for 1.5 hours, 0.7 ml of a dimethylformamide solution of 16 μl (0.146 mmol) of phenylisocyanate was dropwise added to the reaction mixture at −30° C. After stirring at −30° to −20° C. for 30 minutes, 40 μl of 48% hydrogen bromide aqueous solution was added to the reaction mixture followed by stirring at −10° to 0° C. for 15 minutes. The reaction mixture was treated in the conventional manner to give 74 mg of the crude product. The crude product was purified by silica gel column chromatography (10 ml of silica gel, eluting solvent; n-hexane: ethyl acetate=2:1) to give 22.2 mg of Compound 9 (yield; 32.1%).

Physicochemical properties of Compound 9 are as follows.

$^1$H-NMR(CDCl$_3$) δ(ppm); 8.05 (s 1H), 7.32-7.37 (m 5H), 7.15 (m 1H), 6.49 (br 1H), 4.02-4.16 (m 4H), 3.76 (s 3H), 3.50 (m 1H), 1.66 (s 3H).

IR(KBr) $\gamma_{max}$ (cm$^{-1}$); 3370(br), 1732, 1634-1700, 1597, 1531, 1507.

SI-MS m/z; 474, 476(M+1)$^+$, 414, 416, 295, 297, 215.

EXAMPLE 11: SYNTHESIS OF COMPOUND 10

In an argon atmosphere, 7.0 mg (0.175 mmol) of 60% sodium hydride was suspended in 0.6 ml of dimethylformamide. While cooling the suspension at −20° C., 0.7 ml of a dimethylformamide solution containing 40 mg (0.146 mmol) of Compound 18 was dropwise added to the suspension. The mixture was stirred at −20° to −10° C. for 2 hours and 40 minutes. After cooling to −30° C., 0.7 ml of a dimethylformamide solution containing 17 μl (0.146 mmol) of benzoyl chloride was dropwise added to the reaction mixture. After stirring at −30° to −20° C. for 40 minutes, the reaction mixture was treated in the conventional manner to give 53 mg of the crude product. The crude product was purified by silica gel column chromatography (10 ml of silica gel, eluting solvent; chloroform: acetone=1:0-50:1) to give 37.1 mg of Compound 10 (yield; 67.2%).

Physicochemical properties of Compound 10 are as follows.

$^1$H-NMR(CDCl$_3$) δ(ppm); 7.51-7.57 (m 3H), 7.42-7.46 (m 2H), 5.94 (br s 1H), 5.89 (s 1H), 4.20 (dd 1H J=11.7, 5.0 Hz), 4.10 (d 1H J=11.7 Hz), 3.74 (s 3H), 2.98 (ddd 1H) J=7.7, 5.0, 5.0 Hz), 2.35 (dd 1H J=7.7, 3.9 Hz), 1.64 (s 3H), 1.41 (dd 1H J=5.0, 3.9 Hz).

SI-MS m/z; 381(M+3)$^+$, 380(M+2)$^+$, 379(M+1)$^+$, 321.

IR(KBr) γ$_{max}$(cm$^{-1}$); 3260, 1742, 1669, 1617, 1559.

EXAMPLE 12: SYNTHESIS OF COMPOUND 11

Compound 10, 31 mg, was dissolved in 1 ml of acetonitrile and 25 μl of 48% hydrogen bromide aqueous solution was added to the solution followed by stirring at room temperature for an hour. The reaction mixture was treated in the conventional manner. The resulting crude product was purified by silica gel column chromatography (8 ml of silica gel, eluting solvent; n-hexane: ethyl acetate=2:1) to give 20.7 mg of Compound 11 (yield; 55.0%).

Physicochemical properties of Compound 11 are as follows.

$^1$H-NMR(CDCl$_3$) δ(ppm); 10.37 (br s 1H), 8.53 (br s 1H), 7.52-7.61 (m 5H), 5.17 (br 1H), 4.18 (dd 1H J=12.1, 9.8 Hz), 3.97-4.03 (m 2H), 3.88 (dd 1H J=10.1, 3.1 hz), 3.73 (s 3H), 3.61 (dd 1H J=10.1, 7.7 Hz), 1.65 (s 3H).

IR(KBr) γ$_{max}$(cm$^{-1}$); 3362, 3230, 1718, 1648, 1630, 1509, 1402.

SI-MS m/z; 461, 459(M+1)$^+$, 401, 399.

EXAMPLE 13: SYNTHESIS OF COMPOUND 12

In an argon atmosphere, 7.9 mg (0.197 mmol) of 60% sodium hydride was suspended in 0.7 ml of dimethylformamide. While cooling the suspension at −20° C., 0.8 ml of a dimethylformamide solution containing 45 mg (0.164 mmol) of Compound 18 was dropwise added to the suspension. The mixture was stirred at −20° to −10° C. for 2 hours and 40 minutes. After cooling to −30° C., 0.8 ml of a dimethylformamide solution containing 22.3 μl (0.180 mmol) of benzyl isocyanate was dropwise added to the reaction mixture. After stirring at −30° C. for 30 minutes, the reaction mixture was treated in the conventional manner to give 59 mg of the crude product. The crude product was purified by silica gel column chromatography (10 ml of silica gel, eluting solvent; chloroform: acetone=1:0-20:1) to give 34.1 mg of Compound 12 (yield; 51.0%).

Physicochemical properties of Compound 12 are as follows. $^1$NMR(CDCl$_3$) δ(ppm); 7.30-7.38 (m 5H), 6.77 (s 1H), 6.00 (br s 1H), 5.29 (m 1H), 4.50 (dd 1H J=14.5, 5.6 Hz), 4.48 (dd 1H J=14.5, 5.5 Hz), 4.04 (dd 1H J=10.3, 5.2 Hz), 3.94 (d 1H J=10.3 Hz), 3.74 (s 3H), 2.95 (ddd 1H J=7.6, 5.0, 5.0 Hz), 2.15 (dd 1H J=7.6, 3.9 Hz), 1.63 (s 3H), 1.14 (dd 1H J=4.9, 3.9 Hz).

SI-MS m/z; 410(M+3)$^+$, 409(M+2)$^+$, 408(M+1)$^+$.

IR(KBr) γ$_{max}$ (cm$^{-1}$); 1746, 1664, 1611, 1527.

EXAMPLE 14: SYNTHESIS OF COMPOUND 13

In an argon atmosphere, 6.4 mg (0.161 mmol) of 60% sodium hydride was suspended in 0.6 ml of dimethylformamide. While cooling the suspension at −20° C., 0.7 ml of a dimethylformamide solution containing 40 mg (0.146 mmol) of Compound 18 was dropwise added to the suspension. The mixture was stirred at −20° to −10° C. for 2 hours and 10 minutes. After cooling to −30° C., 0.7 ml of a dimethylformamide solution containing 21.3 μl (0.161 mmol) of benzyl isothiocyanate was dropwise added to the reaction mixture After stirring at −30° to −20° C. for 50 minutes, 40 μl of 48% hydrogen bromide aqueous solution was added to the reaction mixture followed by stirring at −20° C. to room temperature for 15 minutes. Citrate buffer of pH 5 was added and the formed precipitates were taken by filtration. After thoroughly washing with water, the precipitates were dried in vacuum to give 52.5 mg of Compound 13 (yield; 71.4%).

Physicochemical properties of Compound 13 are as follows.

$^1$NMR(CDCl$_3$-CD$_3$OD) δ(ppm); 8.44 (s b 1H), 7.28-7.41 (m 5H), 4.93 (d 1H J=14.9 Hz), 4.92 (d 1H J=14.9 Hz) 4.31 (dd 1H J=11.0, 9.1 hz), 4.26 (dd 1H J=11.0, 4.1 Hz), 3.97 (m 1H), 3.94 (dd 1H J=9.7, 3.2 Hz), 3.75 (s 3H), 3.53 (dd 1H J=9.7, 8.5 hz), 1.65 (s 3H).

SI-MS m/z; 506, 504(M+1)$^+$, 399,397, 356. 354, 297, 295.

IR(KBr) γ$_{max}$(cm$^{631\ 1}$); 3350, 1717, 1654, 1630, 1507.

EXAMPLE 15: SYNTHESIS OF COMPOUND b 14

In an argon atmosphere, 6.4 mg (0.161 mmol) of 60% sodium hydride was suspended in 0.6 ml of dimethylformamide. While cooling the suspension to −20° C., 0.7 ml of a dimethylformamide solution containing 40 mg (0.146 mmol) of Compound 18 was dropwise added to the suspension. The mixture was stirred at −20° to −10° C. for 2 hours. After cooling to −30° C., 0.7 ml of a dimethylformamide solution containing 20.2 μl (0.161 mmol) of phenoxyacetyl chloride was dropwise added to the reaction mixture. After stirring at −30° to −20° C. for 25 minutes, the reaction mixture was treated in the conventional manner to give 58 mg of the crude product. The crude product was purified by silica gel column chromatography (10 ml of silica gel, eluting solvent; chloroform) to give 35.8 mg of Compound 14 (yield; 60.1%).

Physicochemical properties of Compound 14 are as follows.

$^1$H-NMR(CDCl$_3$) δ(ppm); 7.31 (m 2H), 7.14 (br 1H), 7.03 (t 1H J=7.4 Hz), 6.92 (m 2H), 6.00 (br s 1H), 4.75 (s 2H), 4.22 (d 1H J=10.8 Hz), 4.13 (dd 1H J=10.8, 5.1 Hz), 3.74 (s 3H), 2.97 (ddd 1H J=7.7, 5.1, 5.0 Hz), 2.17 (dd 1H J=7.6, 4.0 Hz), 1.65 (s 3H), 1.07 (dd 1H J=4.6, 4.0 Hz).

SI-MS m/z; 411(M+3)$^+$, 410(M+2)$^+$, 409(M+1)$^+$, 381, 351, 215.

IR(KBr) γ$_{max}$ (cm$^{-1}$); 1733, 1663, 1627, 1560.

EXAMPLE 16: SYNTHESIS OF COMPOUND 15

Compound 14, 23.5 mg, was dissolved in 0.8 ml of acetonitrile and 20 μl of 48% hydrogen bromide aqueous solution was added to the solution followed by stirring at room temperature for 10 minutes. The reaction mixture was treated in the conventional manner to give 27.4 mg of Compound 15 (yield; 97.3%).

Physicochemical properties of Compound 15 are as follows.

$^1$H-NMR(CDCl$_3$) δ(ppm); 8.43 (s 1H), 7.29 (m 2H), 7.02 (m 3H), 4.77 (d 1H J=14.3 Hz), 4.74 (d 1H J=14.3 Hz), 4.15 (m 1H), 4.05 (dd 1H J=10.9, 4.2 Hz), 3.93-4.00 (m 2H), 3.82 (s 3H), 3.55 (dd 1H J=10.7, 8.9 Hz), 1.69 (s 3H).

EI-MS m/z; 488, 490(M+), 429, 431, 408, 349.
IR(KBr) $\gamma_{max}$ (cm$^{-1}$); 3364, 1733, 1699, 1653, 1625, 1508.

EXAMPLE 17: SYNTHESIS OF COMPOUND 16

In an argon atmosphere, 8.0 mg (0.200 mmol) of 60% sodium hydride was suspended in 0.7 ml of dimethylformamide. While cooling the suspension at −20° C., 0.8 ml of a dimethylformamide solution containing 50 mg (0.182 mmol) of Compound 18 was dropwise added to the suspension. The mixture was stirred at −20° to −10° C. for 2 hours and 25 minutes. After cooling to −30° C., 0.8 ml of a dimethylformamide solution containing 26 μl (0.182 mmol) of benzyl chloroformate was dropwise added to the reaction mixture After stirring at −30° to −20° C. for 35 minutes, the reaction mixture was treated in the conventional manner to give 71 mg of the crude product. The crude product was purified by silica gel column chromatography (10 ml of silica gel, eluting solvent; chloroform) to give 47.6 mg of Compound 16 (yield; 63.9%).

Physicochemical properties of Compound 16 are as follows.

$^1$H-NMR(CDCl$_3$) δ(ppm); 7.34-7.41 (m 5H), 7.00 (br s 1H), 6.08 (br s 1H), 5.26 (s 2H), 4.08 (d 1H J=11.3 Hz), 3.99 (dd 1H J=11.3, 5.2 Hz), 3.73 (s 3H), 2.95 (ddd 1H J=7.7, 5.2, 4.9 Hz), 2.13 (dd 1H J=7.7, 3.8 Hz), 1.64 (s 3H), 1.15 (dd 1H J=4.9, 4.0 Hz).

IR(KBr) $\gamma_{max}$ (cm$^{-1}$); 3300(br), 1730, 1675, 1628, 1566, 1400.

EI-MS m/z; 408(M+), 349.

EXAMPLE 18: SYNTHESIS OF COMPOUND 17

Compound 17 was obtained in 25.7 mg (yield; 33.5%) from 50 mg (0.182 mmol) of Compound 18 in a manner similar to Example 9 except for using 23 μl (0.182 mmol) of benzoyl isocyanate instead of phenyl isocyanate.

Physicochemical properties of Compound 17 are as follows.

$^1$H-NMR(CDCl$_3$) δ8.25 (br s 1H), 7.82 (m 2H), 7.62(m 1H), 7.50 (m 2H), 6.62 (s 1H), 6.00 (br s 1H), 4.21 (dd 1H J=11.1, 4.9 Hz), 4.11 (d 1H J=11.1 Hz), 3.75 (s 3H), 2.97 (ddd 1H J=7.6, 5.0, 4.9 Hz), 2.32 (dd 1 H J=7.6, 3.8 Hz), 1.64 (s 3H), 1.27 (m 1H).

EXAMPLE 19: SYNTHESIS OF COMPOUND 19

Compound a, 48 mg, obtained in Reference Example 1 was dissolved in 0.5 ml of acetic acid and 0.4 ml of 25% hydrogen bromide/acetic acid was added to the solution followed by stirring at room temperature for an hour and 10 minutes. After the reaction solution was concentrated, ether was added to the residue The mixture was ground, filtered and dried to give 38.6 mg of Compound 19 (yield; 87.9%).

Physicochemical properties of Compound 19 are as follows.

$^1$H-NMR(CD$_3$OD) δ(ppm); 8.21 (s 1H), 7.68-7.76 (m 5H), 4.75 (d 1H J=16.0 Hz), 4.70 (d 1H J=16.0 Hz), 4.41 (dd 1H J=10.1, 9.2 Hz), 4.26 (m 1H), 4.21 (dd 1H J=10.2, 4.3 Hz), 4.10 (dd 1H J=10.0, 2.9 Hz), 3.93 (dd 1H J=10 0, 7.1 Hz), 3.85 (s 3H), 1.74 (s 3H).

SI-MS m/z; 488, 490(M-HBr)+, 396, 398, 215.

EXAMPLE 20: SYNTHESIS OF COMPOUND 20

Compound 20 was obtained in 14.4 mg (yield: 67.1%) in a manner similar to Example 8 except for using 18 mg of Compound 17 instead of Compound 6.

Physicochemical properties of Compound 20 are as follows.

$^1$H-NMR(CDCl$_3$) δ(ppm); 7.76-7.83 (m 2H), 7.63 (br s 1H) 7.51-7.56 (m 1H), 7.41-7.48 (m 2H), 4.27 (dd 1H J=10.8, 9.4 Hz), 4.06 (dd 1H J=10.9, 4.1 Hz), 3.99 (m 1H), 3.89 (dd 1H J=10.0, 3.2 Hz), 3.69 (s 3H), 3.52 (dd 1H J=10.0, 8.4 Hz), 1.59 (s 3H).

EI-MS m/z; 421(M-HBr)+, 354, 356, 295, 297, 274, 215, 147.

EXAMPLE 21: SYNTHESIS OF COMPOUND 21

Compound 21 was obtained in 138 mg (yield: 74.8%) from 160 mg (0.58 mmol) of Compound 18 in a manner similar to Example 2 except for using 41 μl (0.58 mmol) of acetyl chloride instead of indole-2-carbonyl chloride.

Physicochemical properties of Compound 21 are as follows.

$^1$H-NMR(CDCl$_3$) δ(ppm); 6.9-7.1 (br 1H), 5.98 (br s 1H) 4.10 (d 1H J=10.8 Hz), 4.03 (dd 1H J=10.8, 4.9 Hz), 3.74 (s 3H), 2.96 (m 1H), 2.27 (s 3H), 2.19 (dd 1H J=7.6, 3.9 Hz), 1.65 (s 3H), 1.14 (dd 1H J=4.8, 3.9 Hz).

EI-MS m/z; 316(M+), 274, 257, 215.

EXAMPLE 22: SYNTHESIS OF COMPOUND 22

Compound 22 was obtained in 130 mg (yield: 64.7%) in a manner similar to Example 8 except for using 160 mg of Compound 21 instead of Compound 6.

Physicochemical properties of Compound 22 are as follows.

$^1$H-NMR(CDCl$_3$) δ(ppm); 10.70 (br s 1H), 8.42 (s 1H), 5.35 (s 1H), 4.22 (dd 1H J=10.0, 8.6 Hz), 4.08 (m 1H), 4.05 (m 1H), 4.02 (dd 1H J=10.2, 3.1 Hz), 3.78 (s 3H), 3.54 (dd 1H J=9.8, 8.5 Hz), 2.32 (s 3H), 1.69 (s 3H).

EI-MS m/z; 396, 398(M+), 337, 339, 316, 257, 215.

EXAMPLE 23: SYNTHESIS OF COMPOUND 23

Compound 23 was obtained in 27.5 mg (yield: 52.7%) from 30 mg (0.109 mmol) of Compound 18 in a manner similar to Example 2 except for using 37.4 mg (0.109 mmol) of p-nitrophenyl 5,6-dimethoxyindole-2-carboxylate instead of indole-2-carbonyl chloride.

Physicochemical properties of Compound 23 are as follows.

1H-NMR(CDCl$_3$) δ(ppm); 9.21 (br 1H), 7.23 (br s 1H), 7.01(s 1H), 6.95 (br s 1H), 6.86 (s 1H), 6.06 (br 1H), 4.43 (m 2H), 3.95 (s 3H), 3.92 (s 3H), 3.75 (s 3H), 3.06 (m 1H), 2.23 (dd 1H J=7.6, 3.9 Hz), 1.67 (s 3H), 1.27 (dd 1H J=4.8, 4.0 Hz).

EI-MS m/z; 477(M+), 407, 288, 227, 215, 213, 204.

EXAMPLE 24: SYNTHESIS OF COMPOUND 24

Compound 24 was obtained in 16.5 mg (yield: 94.1%) in a manner similar to Example 8 except for using 15 mg of Compound 23 instead of Compound 6.

Physicochemical properties of Compound 24 are as follows.

$^1$H-NMR(CDCl$_3$-CD$_3$OD) δ(ppm); 7.99 (s 1H), 7.11 (s 1H), 6.99 (s 1H), 6.95 (s 1H), 4.63 (dd 1H J=10.9, 9.3 Hz), 4.54 (dd 1H J=10.9, 4.2 Hz), 4.16 (m 1H), 4.01 (dd 1H J=10.0, 3.3 Hz), 3.96 (s 3H), 3.94 (s 3H), 3.77 (s 3H), 3.59 (dd 1H J=10.0, 8.6 Hz), 1.68(s 3H).

EI-MS m/z; 557, 559(M+), 477, 354, 356, 274, 213, 204.

EXAMPLE 25: SYNTHESIS OF COMPOUND 25

Compound 25 was obtained in 37.3 mg (yield: 58.9%) from 40 mg (0.146 mmol) of Compound 18 in a manner similar to Example 2 except for using 46 mg (0.153 mmol) of p-nitrophenyl benzothiophene-2-carboxylate instead of indole-2-carbonyl chloride.

Physicochemical properties of Compound 25 are as follows.

$^1$H-NMR(CDCl$_3$) δ(ppm); 7.83-7.88 (m 2H), 7.79 (d 1H J=0.7 Hz), 7.48 (m 1H), 7.43 (m 1H), 6.60 (s 1H), 5.98 (br s 1H), 4.37 (dd 1H J=11.1, 5.0 Hz), 4.27 (d 1H J=11.1 Hz), 3.75 (s 3H), 3.02 (dt 1H J=7.7, 4.9 Hz), 2.34 (dd 1H J=7.7, 3.9 Hz), 1.66 (s 3H), 1.40 (dd 1H J=4.9, 4.1 Hz).

EI-MS m/z; 434(M+), 375, 161.

EXAMPLE 26: SYNTHESIS OF COMPOUND 26

Compound 26 was obtained in 26.7 mg (yield: 86.6%) in a manner similar to Example 8 except for using 26 mg of Compound 25 instead of Compound 6.

Physicochemical properties of Compound 26 are as follows.

$^1$H-NMR(CDCl$_3$-CD$_3$OD) δ(ppm); 7.90-7.93 (m 3H), 7.82 (s 1H), 7.43-7.50 (m 2H), 4.58 (dd 1H J=11.1, 9.2 Hz), 4.47 (dd 1H J=11.1, 4.1 Hz), 4.11 (m 1H), 3.97 (m 1H), 3.76 (s 3H), 3.64 (dd 1H J=10.1, 8.2 Hz), 1.68 (s 3H).

EI-MS m/z; 514, 516(M+), 434(M-HBr)+, 375, 161.

EXAMPLE 27: SYNTHESIS OF COMPOUND 27

Compound 27 was obtained in 50.1 mg (yield: 79.1%) from 40 mg (0.146 mmol) of Compound 18 in a manner similar to Example 2 except for using 46 mg (0.153 mmol) of p-nitrophenyl 3-methoxycinnamate instead of indole-2-carbonyl chloride.

Physicochemical properties of Compound 27 are as follows.

$^1$H-NMR(CDCl$_3$) δ(ppm); 7.80 (d 1H J=15.4 Hz), 7.33 (dd 1H J=8.0, 7.9 Hz), 7.16 (br d 1H J=7.6 Hz), 7.05 (m 1H), 6.97 (ddd 1H J=8.2, 2.6, 0.8 Hz), 6.89 (br 1H), 6.75 (d 1H J=15.4 Hz), 6.01 (br s 1H), 4.23 (d 1H J=11.0 Hz), 4.18 (dd 1H J=11.0, 4.9 Hz), 3.85 (s 3H), 3.75 (s 3H), 2.99 (m 1H), 2.26 (dd 1H J=7.7, 3.9 Hz), 1.66 (s 3H), 1.23 (m 1H).

EI-MS m/z; 434(M+), 375, 274, 161.

EXAMPLE 28: SYNTHESIS OF COMPOUND 28

Compound 28 was obtained in 24.1 mg (yield: 78.1%) in a manner similar to Example 8 except for using 26 mg of Compound 27 instead of Compound 6.

Physicochemical properties of Compound 28 are as follows.

$^1$H-NMR(CD$_3$OD) δ(ppm); 8.12 (s 1H), 7.66 (d 1H J=15.4 Hz), 7.33 (dd 1H J=7.9, 7.8 Hz), 7.25 (br d 1H J=7.8 Hz), 7.22 (br s 1H), 7.06 (d 1H J=15.4 Hz), 6.97 (m 1H), 4.49 (dd 1H J=11.0, 9.9 Hz), 4.32 (dd 1H J=11.0, 4.3 Hz), 4.09 (m 1H), 3.93 (dd 1H J=10.0, 3.0 Hz), 3.85 (s 3H), 3.79 (dd 1H J=9.9, 7.2 Hz), 3.69 (s 3H) 1.57(s 3H).

EXAMPLE 29: SYNTHESIS OF COMPOUND 29

Compound 29 was obtained in 49.1 mg (yield: 72.5%) from 40 mg (0.146 mmol) of Compound 18 in a manner similar to Example 2 except for using 50 mg (0.153 mmol) of p-nitrophenyl 3,4-dimethoxycinnamate instead of indole-2-carbonyl chloride.

Physicochemical properties of Compound 29 are as follows.

$^1$H-NMR(CDCl$_3$) δ(ppm); 7.79 (d 1H J=15.3 Hz), 7.18 (dd 1H J=8.4, 2.0 Hz), 7.04 (d 1H J=2.0 Hz), 6.89 (br 1H), 6.89 (d 1H J=8.4 Hz), 6.62 (d 1H J=15.3 Hz), 6.01 (br s 1H), 4.23 (d 1H J=11.0 Hz) 4.18 (dd 1H J=11.0, 4.8 Hz), 3.934 (s 3H), 3.926 (s 3H), 3.75 (s 3H), 2.99 (m 1H), 2.26 (dd 1H J=7.6, 3.9 Hz), 1.66 (s 3H), 1.23 (dd 1H J=5.0, 3.9 Hz).

EI-MS m/z; 464(M+), 406, 191.

EXAMPLE 30: SYNTHESIS OF COMPOUND 30

Compound 30 was obtained in 17.3 mg (yield: 52.6%) in a manner similar to Example 8 except for using 28 mg of Compound 29 instead of Compound 6.

Physicochemical properties of Compound 30 are as follows.

$^1$H-NMR(CD$_3$OD) δ(ppm); 8.12 (s 1H), 7.64 (d 1H J=15.4 Hz), 7.31 (d 1H J=1.7 Hz), 7.23 (dd 1H J=8.4, 1.9 Hz), 6.99 (d 1H J=8.4 Hz), 6.93 (d 1H J=15.4 Hz), 4.48 (dd 1H J=11.0, 10.2 Hz), 4.32 (dd 1H J=11.0, 4.3 Hz), 4.08 (m 1H), 3.92 (dd 1H J=10.0, 3.0 Hz), 3.79 (dd 1H J=9.9, 7.2 Hz), 3.90 (s 3H), 3.87 (s 3H), 3.69 (s 3H), 1.57 (s 3H).

EI-MS m/z; 544, 546(M+), 464, 405, 191.

EXAMPLE 31: SYNTHESIS OF COMPOUND 31

Compound 31 was obtained in 48.6 mg (yield: 100%) in a manner similar to Example 19 except for using 53 mg of Compound b obtained in Reference Example 2 instead of Compound a.

Physicochemical properties of Compound 31 are as follows.

$^1$H-NMR(DMSO-d$_6$) δ(ppm); 10.16 (br s 1H), 8.00 (s 1H), 7.25 (br 1H), 7.03 (d 1H J=7.1 Hz), 6.95 (dd 1H J=7.4, 7.1 Hz), 6.56-6.60 (m 2H), 4.64 (dd 1H J=10.5, 5.8 Hz), 4.39 (m 1H), 4.00-4.06(m 2H) 3.94(dd 1H J=9.7,2.6 Hz) 3.80(dd 1H J=9.6,7.2 Hz) 3.59(s 3H) 3.48(m 1H) 3.23(m 1H) 1.45(s 3H).

EI-MS m/z: 499, 501, 419, 360, 356, 274, 215.

EXAMPLE 32: SYNTHESIS OF COMPOUND 32

In an argon atmosphere, 8.7 mg (0.22 mmol) of 60% sodium hydride was suspended in 0.8 ml of dimethylformamide. While cooling the suspension to −30° C. and 0.7 ml of a dimethylformamide solution containing 50 mg (0.18 mmol) of Compound 18 was dropwise added to the suspension. The mixture was stirred at −30° to −10° C. for 2 hours. After cooling to −50° C., 1.2 ml of a dimethylformamide solution containing 80 mg (0.20 mmol) of p-nitrophenyl 5-tert-butoxycarbonylaminoindole-2-carboxylate was dropwise added to the reaction mixture. The mixture was stirred at −50° to −30° C. for 50 minutes. The reaction mixture was treated in the conventional manner and the resulting crude product was purified by silica gel column chloroform: acetone=1:0-50:1) to give 54.2 mg of Compound 32 (yield: 55.8%).

Physicochemical properties of Compound 32 are as follows.

$^1$H-NMR(DMSO-d$_6$) δ(ppm); 11.68 (br s 1H), 9.16 (br 1H), 8.70 (s 1H), 7.79 (br s 1H), 7.34 (br s 2H), 7.12 (d 1H J=2.0 Hz), 6.93 (s 1H), 4.57 (dd 1H J=10.6, 5.3 Hz), 4.43 (d 1H J=10.6 Hz), 3.61 (s 3H), 3.01 (m 1H), 1.96 (dd H J=7.6, 3.6 Hz), 1.49 (s 9H), 1.46 (s 3H), 1.43 (dd 1H J=4.8, 3.8 Hz).

SI-MS m/z; 535 (M+3)+, 479.

EXAMPLE 33: SYNTHESIS OF COMPOUND 33

Compound 33 was obtained in 93 mg (yield: 88.9%) from 125 mg of Compound 32 in a manner similar to Example 8 except for using Compound 32 instead of Compound 6.

Physicochemical properties of Compound 33 are as follows.

¹H-NMR (DMSO-d₆) δ(ppm): 11.21 (br s 1H), 10.17 (s 1H), 8.07 (br s 1H), 7.31 (s 1H), 7.20 (d 1H J=8.7 Hz), 6.81 (d 1H J=1.7 Hz), 6.77 (d 1H J=1.8 Hz), 6.68 (dd 1H J=8.7, 2.1 Hz), 4.79 (br 2H), 4.65 (dd 1H J=10.8, 9.7 Hz), 4.33 (dd 1H J=11.0, 4.2 Hz), 4.07 (m 1H), 3.93 (dd 1H J=9.6, 2.8 Hz), 3.82 (dd 1H J=9.7, 7.2 Hz), 3.61 (s 3H), 1.47 (s 3H).

SI-MS m/z; 513, 515 (M+1)⁺.

EXAMPLE 34: SYNTHESIS OF COMPOUND 34

In an argon atmosphere, 4.4 mg (0.11 mmol) of 60% sodium hydride was suspended in 0.5 ml of dimethylformamide. While cooling the suspension to −30° C., 0.5 ml of a dimethylformamide solution containing 25 mg (0.091 mmol) of Compound 18 was dropwise added to the suspension. The mixture was stirred at −30° to −10° C. for 2 hours. After cooling to −50° C., 0.5 ml of a dimethylformamide solution containing 29 mg (0.091 mmol) of p-nitrophenyl 5-methoxybenzofuran-2-carboxylate was dropwise added to the reaction mixture. After stirring at −50° to −30° C. for 40 minutes, 0.025 ml of 47% hydrogen bromide aqueous solution was added to the mixture followed by stirring for further 20 minutes. The reaction mixture was treated in the conventional manner and the resulting crude product was purified by silica gel column chromatography (10 ml of silica gel, eluting solvent; chloroform: acetone=1-:0-50:1) to give 37.8 mg of Compound 34 (yield: 78.3%).

Physicochemical properties of Compound 34 are as follows.

¹H-NMR (CD₃OD) δ(ppm); 8.09 (br 1H), 7.55 (s 1H), 7.54 (d 1H J=9.2 Hz), 7.26 (d 1H J=2.5 Hz), 7.09 (dd 1H J=9.2, 2.6 Hz), 4.71 (dd 1H J=11.2, 9.6 Hz), 4.51 (dd 1H J=11.6, 4.0 Hz), 4.12 (m 1H), 3.94 (dd 1H J=9.9, 3.0 Hz), 3.85 (s 3H), 3.81 (dd 1H J=9.9, 7.3 Hz), 3.68 (s 3H), .56 (s 3H).

EI-MS m/z; 528 530 (M⁺), 448 (M-HBr)⁺, 389 (M-HBr-CO₂CH₃)⁺, 212, 175.

IR (KBr) γ_max (cm⁻¹); 1741, 1700, 1653, 1502, 1420.

EXAMPLE 35: SYNTHESIS OF COMPOUND 35

Compound 35 was obtained in 53.7 mg (yield: 67.8%) from 40 mg of Compound 18 in a manner similar to Example 34 except for using p-nitrophenyl 3-acetoxycinnamate instead of p-nitrophenyl 5-methoxybenzofuran-2-carboxylate.

Physicochemical properties of Compound 35 are as follows.

¹H-NMR (CDCl₃) δ(ppm); 10.83 (br s 1H), 8.52 (s 1H), 7.71 (d 1H J=15.6 Hz), 7.35–7.37 (m 3H), 7.13 (dd 1H J=5.9, 2.7 Hz), 6.81 (d 1H J=15.6 Hz), 5.50 (s 1H), 4.29 (dd 1H J=10.3, 9.9 Hz), 4.19 (dd 1H J=10.8, 4.2 Hz), 3.97–4.02 (m 2H), 3.80 (s 3H), 3.56 (dd 1H J=10.3, 9.6 Hz), 2.33 (s 3H), 1.69 (s 3H).

EI-MS m/z; 542 544 (M⁺), 462 (M-HBr)⁺, 403 (M-HBr-CO₂CH₃)⁺, 354, 356, 274, 212, 214, 147.

IR (KBr) γ_max(cm⁻¹); 1740, 1696, 1646, 1584, 1503, 1419.

EXAMPLE 36: SYNTHESIS OF COMPOUND 36

Compound 36 was obtained in 68.8 mg (yield: 74.4%) from 40 mg of Compound 18 in a manner similar to Example 34 except for using p-nitrophenyl 4-carbobenzoxyaminocinnamate instead of p-nitrophenyl 5-methoxybenzofuran-2-carboxylate.

Physicochemical properties of Compound 36 are as follows.

¹H-NMR (CDCl₃) δ(ppm): 10.62 (br 1H), 8.57 (s 1H), 7.74 (d 1H J=15.5 Hz), 7.57 (d 2H J=8.7 Hz), 7.45 (d 2H J=8.6 Hz), 7.34–7.43 (m 5H), 6.85 (s 1H), 6.78 (d 1H J=15.5 Hz), 5.30 (s 1H), 5.22 (s 2H), 4.39 (dd 1H J=10.5, 9.8 Hz), 4.28 (dd 1H J=10.8, 4.3 Hz), 4.10 (m 1H), 4.03 (dd 1H J=10.0, 3.2 Hz), 3.77 (s 3H), 3.56 (dd 1H J=9.8, 8.9 Hz), 1.69 (s 3H).

EI-MS m/z; 633, 635 (M⁺), 553 (M-HBr)⁺, 525, 527, 445, 386, 274, 212, 172.

IR(KBr) γ_max (cm⁻¹); 3350, 1732, 1697, 1636, 1605, 1589, 1521, 1505, 1414.

EXAMPLE 37: SYNTHESIS OF COMPOUND 37

Compound 37 was obtained in 31.0 mg (yield: 62.7%) from 25 mg of Compound 18 in a manner similar to Example 34 except for using p-nitrophenyl 4-acetamidocinnamate instead of p-nitrophenyl 5-methoxybenzofuran-2-carboxylate.

Physicochemical properties of Compound 37 are as follows.

¹H-NMR (DMSO-d₆) δ(ppm); 10.15 (s 1H), 10.10 (s 1H), 8.16 (s 1H), 7.70 (d 2H J=8.7 Hz), 7.64 (d 2H J=8.7 Hz), 7.55 (d 1H J=15.3 Hz), 7.27 (s 1H), 7.00 (d 1H J=15.3 Hz), 4.47 (dd 1H J=10.5, 10.1 Hz) 4.21 (dd 1H J=10.9, 4.3Hz), 4.06 (m 1H), 3.91 (dd 1H J=9.7, 2.9 Hz), 3.78 (dd 1H J=9.2, 8.3 Hz), 3.60 (s 3H), 2.07 (s 3H), 1.46 (s 3H).

EI-MS m/z; 541, 543 (M⁺), 461 (M-HBr)⁺, 402 (M-HBr-CO₂CH₃)⁺, 272, 212, 188.

IR (KBr) γ_max (cm⁻¹); 3344, 1734, 1678, 1639, 1594, 1506, 1410, 1318, 1260.

EXAMPLE 38: SYNTHESIS OF COMPOUND 38

Compound 38 was obtained in 32.6 mg (yield: 69.4%) from 25 mg of Compound 18 in a manner similar to Example 34 except for using p-nitrophenyl 4-methoxycinnamate instead of p-nitrophenyl 5-methoxybenzofuran-2-carboxylate.

Physicochemical properties of Compound 38 are as follows.

¹H-NMR (CDCl₃) δ(ppm); 10.84 (br s 1H), 8.59 (s 1H), 7.76 (d 1H J=15.5 Hz), 7.58 (d 2H J=8.8 Hz), 6.94 (d 2H J=8.8 Hz), 6.73 (d 1H J=15.5 Hz), 5.31 (s 1H), 4.39 (dd 1H J=10.6, 9.5 Hz), 4.28 (dd 1H J=10.7, 4.3 Hz), 4.08 (m 1H), 4.04 (dd 1H J=9.6, 3.2 Hz), 3.87 (s 3H), 3.78 (s 3H), 3.55 (dd 1H J=9.6, 8.9 Hz), 1.69 (s 3H).

EI-MS m/z; 514, 516 (M⁺), 434 (M-HBr)⁺, 375 (M-HBr-CO₂CH₃)⁺, 354, 356, 161, 133.

IR (KBr) γ_max (cm⁻¹); 3354, 1742, 1698, 1635, 1602, 1508, 1434, 1305, 1251, 1173.

EXAMPLE 39: SYNTHESIS OF COMPOUND 39

Compound 39 was obtained in 34.0 mg (yield: 68.1%) from 25 mg of Compound 18 in a manner similar to Example 34 except for using p-nitrophenyl 3-(3,4-dimethoxyphenyl)propionate instead of p-nitrophenyl 5-methoxybenzofuran-2-carboxylate.

Physicochemical properties of Compound 39 are as follows.

¹H-NMR (CDCl₃) δ(ppm): 10.63 (br s 1H), 8.50 (s 1H), 6.82 (s 2H), 6.78 (s 1H), 5.27 (br s 1H), 4.05 (t 1H J=9.9 Hz), 3.92–4.00 (m 2H), 3.87 (m 1H), 3.86 (s 3H), 3.81 (s 3H), 3.76 (s 3H), 3.31 (dd 1H J=9.6, 8.7 Hz), 3.06 (t 2H J=7.6 Hz), 2.74–2.88 (m 2H), 1.68 (s 3H).

EI-MS m/z; 546, 548 (M+), 466 (M-HBr)+, 407 (M-HBr-CO$_2$CH$_3$)+, 315, 274, 215, 151.

IR (KBr) $\gamma_{max}$ (cm$^{-1}$); 3340, 1743, 1695, 1608, 1508, 1433, 1262.

EXAMPLE 40: SYNTHESIS OF COMPOUND 40

Compound 40 was obtained in 28.2 mg (yield: 58.6%) from 25 mg of Compound 18 in a manner similar to Example 34 except for using 2,4,5-trichlorophenyl 4-dimethylaminocinnamate instead of p-nitrophenyl 5-methoxybenzofuran-2-carboxylate.

Physicochemical properties of Compound 40 are as follows.

$^1$H-NMR (DMSO-d$_6$) δ(ppm); 10.11 (br s 1H), 8.17 (br 1H), 7.58 (d 2H J=8.9 Hz), 7.52 (d 1H J=15.2 Hz), 7.22 (br s 1H), 6.80 (d 1H J=15.2 Hz), 6.73 (d 2H J=8.9 Hz), 4.45 (dd 1H J=10.1, 10.0 Hz), 4.18 (dd 1H J=10.9, 4.4 Hz), 4.05 (m 1H), 3.91 (dd 1H J=9.7, 2.9 Hz), 3.79 (dd 1H J=9.7, 7.6 Hz), 3.60 (s 3H), 2.99 (s 6H), 1.46 (s 3H).

EM-MS m/z; 527, 529 (M+), 447 (M-HBr)+, 388 (M-HBr-CO$_2$CH$_3$)+, 174.

EXAMPLE 41: SYNTHESIS OF COMPOUND 41

Compound 41 was obtained in 30.7 mg (yield: 63.5%) from 25 mg of Compound 18 in a manner similar to Example 34 except for using p-nitrophenyl 4-nitrocinnamate instead of p-nitrophenyl 5-methoxybenzofuran-2-carboxylate.

Physicochemical properties of Compound 41 are as follows.

$^1$H-NMR (DMSO-d$_6$) δ(ppm); 10.18 (s 1H), 8.26 (d 2H J=8.8 Hz), 8.16 (s 1H), 8.07 (d 2H J=8.8 Hz), 7.71 (d 1H J=15.4 Hz), 7.37 (d 1H J=15.4 Hz), 7.33 (s 1H), 4.52 (dd 1H J=10.7, 10.0 Hz), 4.27 (dd 1H J=11.1, 4.5 Hz), 4.08 (m 1H), 3.92 (dd 1H J=9.7, 2.8 Hz), 3.79 (dd 1H J=9.7, 7.7 Hz), 3.60 (s 3H), 1.46 (s 3H).

EI-MS m/z; 529, 531 (M+), 470, 472 (M-CO$_2$CH$_3$)+, 449 (M-HBr)+, 390 (M-HBr-CO$_2$CH$_3$)+, 274, 215, 176, 146.

IR (KBr) $\gamma_{max}$ (cm$^{-1}$); 3364, 1740, 1698, 1646, 1595, 1506, 1435, 1343, 1251.

EXAMPLE 42: SYNTHESIS OF COMPOUND 42

Compound 42 was obtained in 33.2 mg (yield: 71.0%) from 25 mg of Compound 18 in a manner similar to Example 34 except for using p-nitrophenyl 4-formylcinnamate instead of p-nitrophenyl 5-methoxybenzofuran-2-carboxylate.

Physicochemical properties of Compound 42 are as follows.

$^1$H-NMR (DMSO-d$_6$) δ(ppm); 10.19 (s 1H), 10.04 (s 1H), 8.16 (s 1H), 8.01 (d 2H J=8.3 Hz), 7.95 (d 2H J=8.3 Hz), 7.68 (d 1H J=15.4 Hz), 7.33 (br s 1H), 7.32 (d 1H J=15.4 Hz), 4.52 (dd 1H J=10.7, 10.0 Hz), 4.27 (dd 1H J=11.0, 4.5 Hz), 4.08 (m 1H), 3.91 (dd 1H J=9.6, 2.8 Hz), 3.80 (dd 1H J=9.6, 7.6 Hz), 3.60 (s 3H), 1.46 (s 3H).

EI-MS m/z; 512, 514 (M+), 432 (M-HBr)+, 373 (M-HBr-CO$_2$CH$_3$)+, 274, 215, 159.

IR (KBr) $\gamma_{max}$ (cm$^{-1}$); 3360, 1734, 1698, 1635, 1601, 1502, 1432.

EXAMPLE 43: SYNTHESIS OF COMPOUND 43

Compound 43 was obtained in 34.1 mg (yield: 65.0%) from 25 mg of Compound 18 in a manner similar to Example 34 except for using p-nitrophenyl 3,4,5-trimethoxycinnamate instead of p-nitrophenyl 5-methoxybenzofuran-2-carboxylate.

Physicochemical properties of Compound 43 are as follows.

$^1$H-NMR (DMSO-d$_6$) δ(ppm); 10.15 (br s 1H), 8.16 (br s 1H), 7.56 (d 1H J=15.3 Hz), 7.28 (br s 1H), 7.09 (s 2H), 7.05 (d 1H J=15.3 Hz), 4.50 (dd 1H J=10.5, 10.1 Hz), 4.21 (dd 1H J=10.9, 4.3 Hz), 4.10 (br 1H), 3.90 (dd 1H J=9.9, 3.0 Hz), 3.86 (s 6H) (1H overlapped), 3.71 (s 3H), 3.60 (s 3H), 1.46 (s 3H).

EI-MS m/z; 574, 576 (M+), 494 (M-HBr)+, 435 (M-HBr-CO$_2$CH$_3$)+, 354, 356, 221.

EXAMPLE 44: SYNTHESIS OF COMPOUND 44

Compound 44 was obtained in 24.1 mg (yield: 50.9%) from 25 mg of Compound 18 in a manner similar to Example 34 except for using p-nitrophenyl 4-chlorocinnamate instead of p-nitrophenyl 5-methoxybenzofuran-2-carboxylate.

Physicochemical properties of Compound 44 are as follows.

EI-MS m/z; 518, 520 (M+), 438 (M-HBr)+, 379 (M-HBr-CO$_2$CH$_3$)+, 274, 215, 165.

EXAMPLE 45: SYNTHESIS OF COMPOUND 45

Compound 33, 25 mg (0.049 mmol), was dissolved in 4 ml of acetonitrile and 21 mg (0.074 mmol) of p-nitrophenyl indole-2-carboxylate and 4 mg of 4-dimethylaminopyridine were added to the solution followed by stirring at room temperature for 24 hours. After adding 5 mg of p-nitrophenyl indole-2-carboxylate to the reaction mixture, the mixture was stirred for further 3 hours and 30 minutes. The reaction mixture was treated in the conventional manner. The resulting crude product was purified by silica gel column chromatography (15 ml of silica gel, eluting solvent; chloroform: acetone=1:0–100:1) to give 19.3 mg of Compound 45 (yield: 60.4%).

Physicochemical properties of Compound 45 are as follows.

$^1$H-NMR (CD$_3$OD) δ(ppm); 8.50 (br s 1H), 7.70 (d 1H J=8.2 Hz), 7.49 (dd 1H J=8.3, 0.9 Hz), 7.48 (t 1H J=0.9 Hz), 7.32 (ddd 1H J=8.3, 7.1, 1.1 Hz), 7.28 (d 1H J=8.7 Hz), 7.13 (ddd 1H J=8.0, 7.1, 1.0 Hz), 7.03 (dd 1H J=2.1, 0.5 Hz), 6.93 (s 1H), 6.85 (dd 1H J=8.7, 2.1Hz), 4.69 (dd 1H J=11.0, 9.6 Hz), 4.55 (dd 1H J=11.0, 4.4 Hz), 4.20 (m 1H), 3.96 (dd 1H J=10.1, 3.1 Hz), 3.84 (dd 1H J=10.1, 7.2 Hz), 3.71 (s 3H), 1.59 (s 3H).

SI-MS m/z; 656, 658 (M+1)+.

IR (KBr) $\gamma_{max}$ (cm$^{-1}$); 3344, 1715 (br), 1617, 1523, 1490, 1408, 1238, 1176.

EXAMPLE 46: SYNTHESIS OF COMPOUND 46

Compound 46 was obtained in 26.0 mg (yield: 67.7%) from 16.5 mg of Compound 33 in a manner similar to Example 45 except for using p-nitrophenyl benzofuran-2-carboxylate instead of p-nitrophenyl indole-2-carboxylate.

Physicochemical properties of Compound 46 are as follows.

$^1$H-NMR (CDCl$_3$) δ(ppm); 9.23 (br 1H), 8.64 (s 1H), 7.81 (d 1H J=0.9 Hz), 7.77 (m 1H), 7.65 (dd 1H J=8.5, 0.8 Hz), 7.54 (ddd 1H J=8.4, 7.3, 1.3 Hz), 7.38 (ddd 1H J=8.0, 7.3, 0.9 Hz), 7.27 (d 1H J=8.6 Hz), 6.96 (d 1H J=2.1 Hz), 6.88 (d 1H J=1.4 Hz), 6.81 (dd 1H J=8.7, 2.2 Hz), 5.32 (s 1H), 4.66 (dd 1H J=10.8, 9.3 Hz), 4.61 (dd 1H J=10.8, 4.6 Hz), 4.26 (m 1H), 4.05 (dd 1H J=10.1, 3.3 Hz), 3.79 (s 3H), 3.66 (dd 1H J=10.0, 8.7 Hz), 1.70 (s 3H).

SI-MS m/z; 657, 659 (M+1)+, 498, 500 (M+1-CO$_2$CH$_3$)+.

IR (KBr) $\gamma_{max}$ (cm$^{-1}$); 3370, 1741, 1629, 1521, 1491, 1411, 1293, 1170.

EXAMPLE 47: SYNTHESIS OF COMPOUND 47

Compound 47 was obtained in 19.3 mg (yield: 57.7%) from 25 mg of Compound 33 in a manner similar to Example 45 except for using p-nitrophenyl 5-methoxyindole-2-carboxylate instead of p-nitrophenyl indole-2-carboxylate.

Physicochemical properties of Compound 47 are as follows.

SI-MS m/z; 686 688 (M+1)+.

IR (KBr) $\gamma_{max}$ (cm$^{-1}$); 3344, 1717, 1623, 1525, 1491, 1420, 1209, 1179.

EXAMPLE 48: SYNTHESIS OF COMPOUND 48

Compound 36, 30 mg, was dissolved in 1 ml of acetic acid and 0.2 ml of 25% hydrogen bromide/acetic acid was added to the solution. The mixture was stirred at room temperature for 4 hours and 30 minutes. The reaction solution was concentrated and the residue was treated in the conventional manner. The resulting crude product was purified by silica gel column chromatography (10 ml of silica gel; eluting solvent; chloroform: acetone=1:0-10:1) to give 18.9 mg (yield: 79.9%) of Compound 48.

Physicochemical properties of Compound 48 are as follows.

SI-MS m/z; 500, 502 (M+1)+.

IR (KBr) $\gamma_{max}$ (cm$^{-1}$): 3372, 1734, 1700, 1628, 1603, 1502, 1437, 1261.

EXAMPLE 49: SYNTHESIS OF COMPOUND 49

Compound 49 was obtained in 14.2 mg (yield: 44.2%) from 25 mg of Compound 48 in a manner similar to Example 45 except for using Compound 48 instead of Compound 33.

Physicochemical properties of Compound 49 are as follows.

$^1$H-NMR (DMSO-d$_6$) $\delta$(ppm); 12.17 (br s 1H), 8.50 (br s 1H), 7.93 (s 1H), 7.74 (d 1H J=7.9 Hz), 7.46–7.54 (m 3H), 7.45 (d 2H J=8.5 Hz), 7.33 (t 1H J=7.2 Hz), 7.14 (t 1H J=7.2 Hz), 6.75 (d 1H J=15.2 Hz), 6.58 (d 2H J=8.5 Hz), 5.69 (br s 2H), 4.53 (dd 1H J=10.0, 9.9 Hz), 4.27 (m 1H), 4.23 (m 1H), 3.96 (m 2H), 3.62 (s 3H), 1.48 (s 3H).

SI-MS m/z; 643, 645 (M+1)+.

IR (KBr) $\gamma_{max}$ (cm$^{-1}$); 3364, 1733 (br), 1635, 1594, 1516, 1490, 1433, 1309, 1263, 1175, 1144.

EXAMPLE 50: SYNTHESIS OF COMPOUND 50

Compound 50 was obtained in 14.8 mg (yield: 42.9%) from 25 mg of Compound 48 in a manner similar to Example 45 except for using p-nitrophenyl 3,4-dimethoxycinnamate instead of p-nitrophenyl indole-2-carboxylate and using Compound 48 instead of Compound 33.

Physicochemical properties of Compound 50 are as follows.

$^1$H-NMR (CDCl$_3$) $\delta$(ppm); 8.58 (br 1H), 7.89 (d 1H J=15.9 Hz), 7.74 (d 1H J=15.2 Hz), 7.43 (d 2H J=8.5 Hz), 7.20 (dd 1H J=8.4, 1.9 Hz), 7.13 (d 1H J=1.9 Hz), 6.92 (d 1H J=8.4 Hz), 6.68 (d 2H J=8.5 Hz), 6.62 (d 1H J=15.2 Hz), 6.52 (d 1H J=15.9 Hz), 5.20 (s 1H), 4.42 (dd 1H J=10.5, 9.7 Hz), 4.34 (dd 1H J=10.7, 4.5 Hz), 4.19 (m 1H), 4.05 (dd 1H J=9.9, 3.2 Hz), 3.96 (s 3H), 3.95 (s 3H), 3.78 (s 3H), 3.58 (dd 1H J=9.7, 9.4 Hz), 1.67 (s 3H).

EXAMPLE 51: SYNTHESIS OF COMPOUND 51

Compound 51 was obtained in 37.3 mg (yield: 72.7%) from 25 mg of Compound 18 in a manner similar to Example 32 except for using p-nitrophenyl 4-(indole-2-carbonylamino) cinnamate instead of p-nitrophenyl 5-tert-butoxyarbonylaminoindole-2-carboxylate.

Physicochemical properties of Compound 51 are as follows.

$^1$H-NMR (DMSO-d$_6$) $\delta$(ppm); 11.76 (d 1H J=1.7 Hz), 10.39 (s 1H), 8.68 (s 1H), 7.92 (d 2H J=8.8 Hz), 7.81 (d 2H J=8.8 Hz), 7.69 (d 1H J=15.3 Hz), 7.69 (m 1H), 7.48 (dd 1H J=8.3, 0.8 Hz), 7.46 (d 1H J=2.2 Hz), 7.24 (ddd 1H J=8.2, 7.0, 1.2 Hz), 7.13 (br 1H), 7.08 (ddd 1H J=7.9, 7.0, 0.9 Hz), 7.00 (d 1H J=15.4 Hz), 4.41 (d 1H J=10.7 Hz), 4.30 (dd 1H J=10.6, 5.3 Hz), 3.61 (s 3H), 3.01 (ddd 1H J=7.6, 5.1, 5.0 Hz), 1.93 (dd 1H J=7.6, 3.5Hz), 1.46 (s 3H), 1.32 (dd 1H J=4.7, 3.6 Hz).

SI-MS m/z; 565 (M+3)+.

EXAMPLE 52: SYNTHESIS OF COMPOUND 52

Compound 52 was obtained in 29.8 mg (yield: 70.9%) from 20 mg of Compound 18 in a manner similar to Example 32 except for using 2,4,5-trichlorophenyl 5-(indole-2-carbonylamino)benzofuran-2-carboxylate instead of p-nitrophenyl 5-tert-butoxycarbonylaminoindole-2-carboxylate.

Physicochemical properties of Compound 52 are as follows.

$^1$H-NMR (DMSO-d$_6$) $\delta$(ppm); 11.74 (d 1H J=1.6 Hz), 10.36 (s 1H), 8.73 (s 1H), 8.35 (d 1H J=2.0 Hz), 7.87 (dd 1H J=9.0, 2.1 Hz), 7.86 (s 1H), 7.73 (d 1H J=9.0 Hz), 7.69 (d 1H J=7.9 Hz), 7.49 (dd 1H J=8.2, 0.6 Hz), 7.44 (d 1H J=1.6 Hz), 7.23 (m 1H), 7.08 (m 1H), 6.94 (s 1H), 4.55 (m 2H), 3.62 (s 3H), 3.05 (m 1H), 1.98 (dd 1H J=7.6, 3.6 Hz), 1.47 (s 3H) (1H overlapped).

SI-MS m/z; 579 (M+3)+.

IR(KBr) $\gamma_{max}$ (cm$^{-1}$); 1734, 1652, 1540, 1387, 1307, 1240.

EXAMPLE 53: SYNTHESIS OF COMPOUND 53

Compound 53 was obtained in 32.1 mg (yield: 78.5%) from 25 mg of Compound 18 in a manner similar to Example 32 except for using 3,4-methylenedioxycinnamoyl chloride instead of p-nitrophenyl 5-tert-butoxycarbonylaminoindole-2-carboxylate.

Physicochemical properties of Compound 53 are as follows.

$^1$H-NMR (DMSO-d$_6$) $\delta$(ppm); 8.68 (s 1H), 7.62 (d 1H J=15.3 Hz), 7.50 (d 1H J=1.1 Hz), 7.25 (dd 1H J=8.0, 1.1 Hz), 7.12 (br s 1H), 6.97 (d 1H J=8.0 Hz), 6.93 (d 1H J=15.3 Hz), 6.09 (s 2H), 4.39 (d 1H J=10.8 Hz), 4.26 (dd 1H J=10.8, 5.2 Hz), 3.60 (s 3H), 2.99 (m 1H), 1.92 (dd 1H J=7.5, 3.4 Hz), 1.45 (s 3H), 1.29 (t 1H J=4.1 Hz).

EI-MS m/z; 448 (M+), 404, 227, 175, 148.

EXAMPLE 54: SYNTHESIS OF COMPOUND 54

Compound 54 was obtained in 62.0 mg (yield: 72.8%) from 40 mg of Compound 18 in a manner similar to Example 32 except for using p-nitrophenyl 6-benzyloxy-5,7-dimethoxyindole-2-carboxylate instead of p-nitrophenyl 5-tert-butoxycarbonylaminoindole-2-carboxylate.

Physicochemical properties of Compound 54 are as follows.

$^1$H-NMR (CDCl$_3$) δ(ppm); 9.24 (br s 1H), 7.49–7.52 (m 2H), 7.33–7.40 (m 3H), 7.17 (s 1H), 6.94 (d 1H J=2.4 Hz), 6.79 (s 1H), 6.03 (br s 1H), 5.08 (s 2H), 4.45 (dd 1H J=10.1, 4.8 Hz), 4.41 (d 1H J=10.0 Hz), 4.04 (s 3H), 3.88 (s 3H), 3.75 (s 3H), 3.06 (m 1H), 2.25 (dd 1H J=7.6, 4.0 Hz), 1.67 (s 3H), 1.29 (dd 1H J=4.6, 4.1 Hz).

EI-MS m/z; 583 (M+), 549, 492, 311, 272, 220.

EXAMPLE 55: SYNTHESIS OF COMPOUND 55

Compound 55 was obtained in 43.6 mg (yield: 78.1%) from 49 mg of Compound 54 in a manner similar to Example 8 except for using Compound 54 instead of Compound 6.

Physicochemical properties of Compound 55 are as follows.

$^1$H-NMR (CDCl$_3$) δ(ppm); 9.53 (br s 1H), 9.48 (br s 1H), 8.51 (s 1H), 7.52–7.55 (m 2H), 7.31–7.42 (m 3H), 7.02 (d 1H J=2.4 Hz), 6.89 (s 1H), 5.38 (s 1H), 5.11 (s 2H), 4.64 (dd 1H J=10.8, 9.3Hz), 4.55 (dd 1H J=10.9, 4.4 Hz), 4.19 (m 1H), 4.11 (s 3H), 4.05 (dd 1H J=10.0, 3.3 Hz), 3.91 (s 3H), 3.75 (s 3H), 3.61 (dd 1H J=10.0, 8.8 Hz), 1.71 (s 3H).

EI-MS m/z; 663, 665 (M+), 633, 635, 583 (M-HBr)+, 492, 280.

IR (KBr) γ$_{max}$ (cm$^{-1}$); 3330, 1740, 1699, 1610, 1584, 1498, 1420, 1307.

EXAMPLE 56: SYNTHESIS OF COMPOUND 56

Compound 56 was obtained in 22.3 mg (yield: 56%) from 25 mg of Compound 18 in a manner similar to Example 32 except for using p-nitrophenyl p-methoxyphenoxyacetate instead of p-nitrophenyl 5-tert-butoxycarbonylaminoindole-2-carboxylate.

Physicochemical properties of Compound 56 are as follows.

$^1$H-NMR (CDCl$_3$) δ(ppm); 7.14 (br 1H), 6.87 (d 2H J=8.9 Hz), 6.84 (d 2H J=8.9 Hz), 5.99 (br s 1H), 4.70 (s 2H), 4.21 (d 1H J=10.8 Hz), 4.12 (dd 1H J=10.8, 5.0 Hz), 3.77 (s 3H), 3.74 (s 3H), 2.97 (dt 1H J=7.6, 4.9 Hz), 2.17 (dd 1H J=7.6, 3.9 Hz), 1.65 (s 3H), 1.08 (dd 1H J=4.6, 4.2 Hz).

EI-MS m/z; 438 (M+), 379 (M-CO$_2$CH$_3$)+, 315, 287, 255, 215.

EXAMPLE 57: SYNTHESIS OF COMPOUND 57

Compound 57 was obtained in 20.5 mg (yield: 43.3%) from 25 mg of Compound 18 in a manner similar to Example 32 except for using p-nitrophenyl 4-tert-butoxycarbonylaminocinnamate instead of p-nitrophenyl 5-tert-butoxycarbonylaminoindole-2-carboxylate.

Physicochemical properties of Compound 57 are as follows.

$^1$H-NMR (CDCl$_3$) δ(ppm); 7.78 (d 1H J=15.4 Hz), 7.50 (d 2H J=8.7 Hz), 7.42 (d 2H J=8.7 Hz), 6.90 (br 1H), 6.67 (s 1H), 6.67 (d 1H J=15.4 Hz), 6.04 (s 1H), 4.23 (d 1H J=11.0 Hz), 4.18 (dd 1H J=11.1, 4.9 Hz), 3.75 (s 3H), 2.98 (m 1H), 2.25 (dd 1H J=7.6, 3.9 Hz), 1.66 (s 3H), 1.53 (s 9H), 1.22 (t 1H J=4.5 Hz).

EI-MS m/z; 519 (M+), 447, 419, 290, 234, 190, 146.

IR (KBr) γ$_{max}$ (cm$^{-1}$); 1733, 1669, 1589, 1519, 1413, 1390, 1319, 1228, 1158.

EXAMPLE 58: SYNTHESIS OF COMPOUND 58

Compound 58 was obtained in 26.5 mg (yield: 60.9%) from 25 mg of Compound 18 in a manner similar to Example 32 except for using p-nitrophenyl 4-methoxycarbonylaminocinnamate instead of p-nitrophenyl 5-tert-butoxycarbonylaminoindole-2-carboxylate.

Physicochemical properties of Compound 58 are as follows.

EI-MS m/z; 477 (M+), 445, 386, 272, 204, 172.

IR (KBr) γ$_{max}$ (cm$^{-1}$); 1736, 1668, 1593, 1522, 1413, 1389, 1320, 1225.

EXAMPLE 59: SYNTHESIS OF COMPOUND 59

Compound 59 was obtained in 36.4 mg (yield: 81.4%) from 25 mg of Compound 18 in a manner similar to Example 32 except for using p-nitrophenyl 5-(3,4-dimethoxyphenyl)-2,4-pentadienoate instead of p-nitrophenyl 5-tert-butoxycarbonylaminoindole-2-carboxylate Physicochemical properties of Compound 59 are as follows.

$^1$H-NMR (CDCl$_3$) δ(ppm); 7.96 (dd 1H J=15.5, 11.3 Hz), 7.06–7.10 (m 2H), 6.79–6.91 (m 4H), 5.99 (br s 1H), 5.94 (d 1H J=11.3 Hz), 4.15 (d 1H J=11.3 Hz), 4.11 (dd 1H J=11.0, 4.6 Hz), 3.93 (s 3H), 3.91 (s 3H), 3.75 (s 3H), 2.96 (m 1H), 2.23 (dd 1H J=7.6, 3.8 Hz), 1.65 (s 3H), 1.20 (t 1H J=4.4 Hz).

EI-MS m/z; 490 (M+), 431 (M-CO$_2$CH$_3$)+, 217, 185.

IR (KBr) γ$_{max}$ (cm$^{-1}$); 1735, 1669, 1577, 1507, 1380, 1267.

EXAMPLE 60: SYNTHESIS OF COMPOUND 60

Compound 60 was obtained in 31.2 mg (yield: 79.5%) from 25 mg of Compound 18 in a manner similar to Example 32 except for using p-nitrophenyl 5-phenyl-2,4-pentadienoate instead of p-nitrophenyl 5-tert-butoxycarbonylaminoindole-2-carboxylate.

Physicochemical properties of Compound 60 are as follows.

$^1$H-NMR (CDCl$_3$) δ(ppm); 8.05 (ddd 1H J=15.6, 11.4, 0.9 Hz), 7.52–7.55 (m 2H), 7.31–7.38 (m 3H), 6.90 (d 1H J=15.7 Hz), 6.84 (t 1H J=11.4 Hz) (1H overlapped), 6.04 (br s 1H), 5.99 (d 1H J=11.2 Hz), 4.16 (d 1H J=10.7 Hz), 4.11 (dd 1H J=11.2, 4.8 Hz), 3.74 (s 3H), 2.96 (m 1H), 2.24 (dd 1H J=7.6, 3.8 Hz), 1.66 (s 3H), 1.20 (dd 1H J=4.8, 4.1 Hz).

EI-MS m/z; 430 (M+), 371 (M-CO$_2$CH$_3$)+, 157.

EXAMPLE 61: SYNTHESIS OF COMPOUND 61

Compound 61 was obtained in 28.5 mg (yield: 65%) from 25 mg of Compound 18 in a manner similar to Example 32 except for using p-nitrophenyl 4-methoxy-5-nitrocinnamate instead of p-nitrophenyl 5-tert-butoxycarbonylaminoindole-2-carboxylate.

Physicochemical properties of Compound 61 are as follows.

$^1$H-NMR (CDCl$_3$) δ(ppm); 8.06 (d 1H J=2.3 Hz)., 7.77 (d 1H J=15.4 Hz), 7.71 (dd 1H J=8.8, 2.3 Hz), 7.14 (d 1H J=8.8 Hz), 6.88 (br 1H), 6.72 (d 1H J=15.4 Hz), 6.00 (br s 1H), 4.24 (d 1H J=10.8 Hz), 4.19 (dd 1H J=10.9, 4.8 Hz), 4.02 (s 3H), 3.75 (s 3H), 3.01 (dt 1H J=7.5, 4.7 Hz), 2.28 (dd 1H J=7.6, 3.9 Hz), 1.66 (s 3H), 1.23 (dd 1H J=4.9, 4.0 Hz).

REFERENCE EXAMPLE 1: SYNTHESIS OF COMPOUND a

Compound a having the following structural formula was obtained in 69.5 mg (yield: 61.2%) from 50 mg (0.182 mmol) of Compound 18 in a manner similar to Example 10 except for using 81 mg (0.20 mmol) of p-nitrophenyl N-benzyloxycarbonyl-N-phenylglycinate instead of phenylisocyanate.

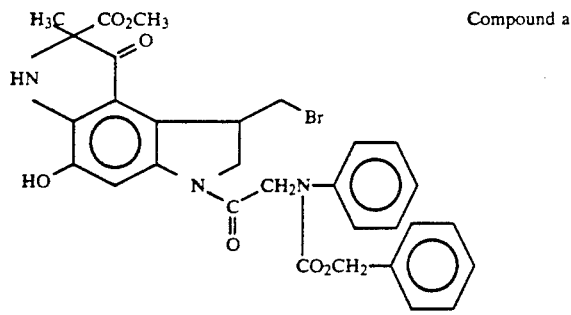

Compound a

Physicochemical properties of Compound a are as follows.

$^1$H-NMR(CDCl$_3$) δ(ppm); 9.34 (br 1H), 8.30 (s 1H), 7.43–7.45 (m 2H), 7.36 (m 2H), 7.22–7.28 (m 6H), 5.26 (br 2H), 4.99 (br s 1H), 4.60 (d 1H J=17.0 Hz), 4.53 (d 1H J=17.0 Hz), 4.17 (br 1H), 3.9-4.1 (br 3H), 3.70 (s 3H), 3.46 (br 1H), 1.49 (s 3H).

EI-MS m/z; 621, 623 (M$^+$), 541 (M-HBr)$^+$, 353, 355, 305.

REFERENCE EXAMPLE 2: SYNTHESIS OF COMPOUND b

Compound b having the following structural formula was obtained in 92.1 mg (yield: 79.6%) from 50 mg (0.18 mmol) of Compound 18 in a manner similar to Example 10 except for usig 80 mg (0.19 mmol) of p-nitrophenyl N-benzyloxycarbonylindoline-2-carboxylate instead of phenyl

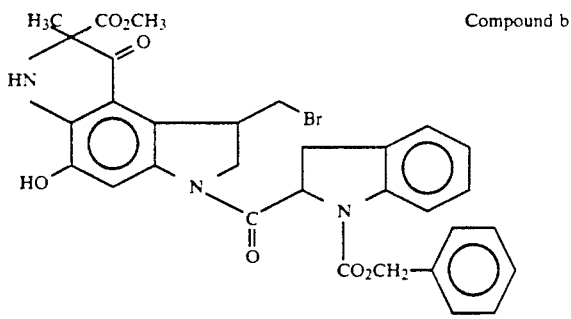

Compound b

Physicochemical properties of Compound b are as follows.

$^1$H-NMR(CDCl$_3$) δ(ppm); 9.45 (br 1H), 8.22 (s 1H), 8.06 (d 1H J=8.0 Hz) 7.32 (m 2H), 7.17 (d 1H J=7.5 Hz), 6.99 7.08 (m 4H), 6.93 (m 2H), 5.12 (d 1H J=11.6 Hz), 5.12 (m 1H), 5.01 (d 1H J=11.6 Hz), 4.14 (br 1H), 3.82-3.92 (m 2H), 3.80 (s 3H), 3.58-3.65 (m 2H), 3.50 (m 1H), 3.24 (dd 1H J=16.3, 5.6 Hz), 1.65 (s 3H).

EI-MS m/z; 633, 635 (M$^+$), 553 (M-HBr)$^+$, 494, 418, 364, 305, 273, 215.

PHARMACEUTICAL PREPARATION 1: (INJECTION)

Compound 46 (10 mg) was dissolved in 50 ml of ethanol, and after stirring, ethanol was removed under reduced pressure. The residue thus obtained was dissolved in 1 l of sterile physiological saline solution. The solution was filtered through a membrane filter with pore size of 0.22 μ (Millipore Inc, FGLD 14200) under a nitrogen gas pressure of 0.5 kg/cm$^2$. The filtrate was poured in 20 ml ampules (10 ml in each), and each ampule was sealed in a conventional manner to prepare injections.

PHARMACEUTICAL PREPARATION 2: (TABLET)

Tablets were prepared from 10 mg of Compound 46, 200 mg of lactose, 40 mg of corn starch, 4 mg of polyvinyl alcohol, 28 mg of Avicel and 1 mg of magnesium stearate.

What is claimed is:

1. A DC-88A derivative represented by formula:

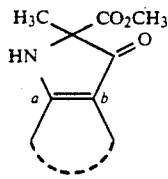

wherein

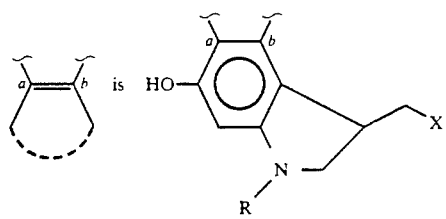

wherein X is chlorine, bromine or iodine; R is hydrogen or a member selected from the group consisting of:

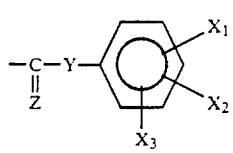

(a)

wherein each of $X_1$, $X_2$, and $X_3$ independently represents hydrogen, —OH, —CHO, —OR$_1$, —OCOR$_1$, —NO$_2$, —NH$_2$, —NR$_2$R$_3$, —NR$_2$COR$_1$, —NHCO$_2$R$_1$, —NHCONH$_2$, —SH, —SR$_1$, —SCOR$_1$, (wherein R$_1$ represents a straight or branched alkyl having 1 to 7 carbon atoms or benzyl and each of R$_2$ and R$_3$ represents hydrogen or R$_1$, and R$_1$ has the same significance as described above), chlorine or bromine; or X$_1$ and X$_2$ are combined to represent —OCH$_2$O—; Z is O, S or NH; Y is —CH$_2$—l (wherein l is an integer of 0 to 7), —(CH=CH)—$_m$ (wherein m is an integer of 1 or 2), —Y'—, —Y'—(CH$_2$)$_n$—, —(CH$_2$)$_n$—Y'—, or

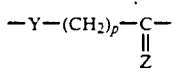

(wherein Y'is O, S or NH, n is an integer from 1 to 4, Z has the same significance as described above and p represents an integer of 0 to 4);

(b) 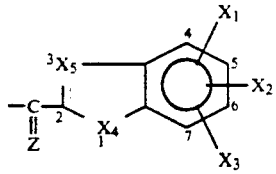

wherein each of $X_1$, $X_2$, $S_3$ and Z have the same significances as described above; $X_4$ is O, S, NH or $NR_1$ (wherein $R_1$ has the same significance as described above); and $X_5$ is —N=, —CH= or —CH$_2$—, provided that when X is Cl or Br and $X_1$, $X_2$, $X_3$ are 5—OCH$_3$, 6—OCH$_3$ and 7—OCH$_3$, respectively and Z is O and $X_4$ is —NH—, $X_5$ is =N— or —CH$_2$—;

(c) 

wherein $R_4$ is a straight or branched alkyl having 1 to 7 carbon atoms or an alkyl wherein any one of the hydrogen atoms in the alkyl is substituted with $X_1$, and $X_1$ has the same significance as described above;

(d) —$R_5$—$R_6$ wherein $R_5$ is selected from the group consisting of (a) (b) and (c) as described above wherein at least one of $X_1$, $X_2$ and $X_3$ is a divalent group remaining after the removal of hydrogen from NH$_2$, and $R_6$ is selected from the group consisting of (a), (b) and (c) as described above;

(e) a group remaining after removal of the hydroxy from the carboxyl in an α amino acid selected from the group consisting of: glycine, alanine, leucine, glutamic acid, aspartic acid, lysine, serine, proline, phenylalanine, tyrosine, tryptophan and histidine; and (f) a benzyloxycarbonyl group or a tert-butoxycarbonyl group.

2. A compound according to claim 1, wherein R represents

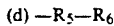

and X represents bromine.

3. A compound according to claim 2, wherein each of $X_1$, $X_2$ and $X_3$ independently represents hydrogen, —OCH$_3$, —OCOCH$_3$, —NO$_2$, —NH$_2$, —N(CH$_3$)$_2$, —NHCOCH$_3$, —NHCO$_2$CH$_2$C$_6$H$_5$ or Cl; and Y is selected from the group consisting of single bond, —CH=CH—, —NH—, —NHCH$_2$—, —CH$_2$O—, —CH$_2$NH— and —NHCO—; Z represents O or S.

4. A compound according to claim 1, wherein R represents

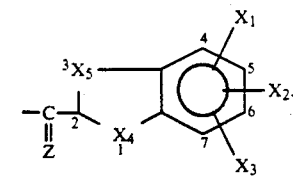

5. A compound according to claim 1, wherein R represents

and X represents bromine.

6. A compound according to claim 5, wherein $R_4$ represents methyl, and Z represents O.

7. A compound according to claim 1, wherein R represents —$R_5$—$R_6$.

8. A compound according to claim 7, wherein $R_5$ represents

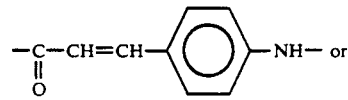

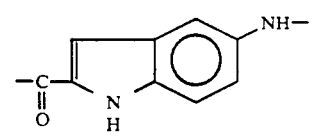

and $R_6$ represents

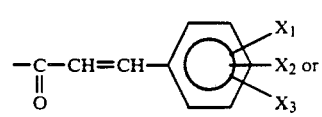

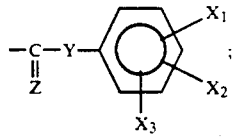

9. A compound according to claim 8, wherein $X_1$, $X_2$ and $X_3$ independently represents hydrogen or methoxy; and $X_4$ represents —NH— or —O—.

10. A pharmaceutical composition comprising a pharmaceutical carrier and, as an active ingredient, an effective antitumor amount of DC-88A derivatives as defined by claim 1.

* * * * *

UNITED STATES PATENT AND TRADEMARK OFFICE
CERTIFICATE OF CORRECTION

PATENT NO. : 5,084,468
DATED : January 28, 1992
INVENTOR(S) : HIROMITSU SAITO, ET AL.

Page 1 of 5

It is certified that error appears in the above-identified patent and that said Letters Patent is hereby corrected as shown below:

COLUMN 1

Line 7, "compound" should read --compounds--.
Line 15, insert: --¶ DC-88A has the following structure.--.

COLUMN 2

Line 15, " 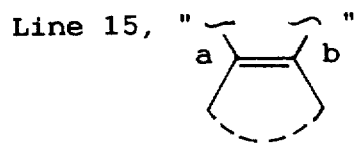 should 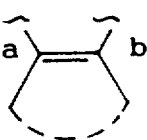 represents--.

Line 62, "—OCH$_2$)—;" should read -- —OCH$_2$—;--.
Line 63, "—CH$_2$—$_1$" should read -- $\text{-(CH}_2\text{)}_1\text{-}$-- and close up right margin.
Line 64, "—CH=CH—$_m$" should read -- $\text{-(CH=CH)}_m\text{-}$--.

COLUMN 5

Line 29, "(IIO" should read --(II)--.

COLUMN 6

Line 23, "or I. As" should read --or I. ¶ As--.

COLUMN 25

Line 57, "cells" should read --Cells--.
Line 58, "3x104 cells/ml" should read --3x10$^4$ cells/ml--.

COLUMN 27

Line 34, "Toxity" should read --Toxicity--.

UNITED STATES PATENT AND TRADEMARK OFFICE
CERTIFICATE OF CORRECTION

PATENT NO. : 5,084,468

DATED : January 28, 1992

INVENTOR(S) : HIROMITSU SAITO, ET AL.

It is certified that error appears in the above-identified patent and that said Letters Patent is hereby corrected as shown below:

COLUMN 29

Line 7, "$\gamma_{max}(sm^{-1})$" should read --$\nu_{max}(cm^{-1})$--.
Line 38, "$\gamma_{max}(cm^{-1})$" should read --$\nu_{max}(cm^{-1})$--.
Line 61, "$\gamma_{max}(cm^{-1})$" should read --$\nu_{max}(cm^{-1})$--.

COLUMN 30

Line 27, "$\gamma_{max}(cm^{-1})$" should read --$\nu_{max}(cm^{-1})$--.
Line 61, "$\gamma_{max}(cm^{-1})$" should read --$\nu_{max}(cm^{-1})$--.

COLUMN 31

Line 44, "$407(M+3)^3$" should read --$407(M+3)^+$--.
Line 45, "$\gamma_{max}(cm^{-1})$" should read --$\nu_{max}(cm^{-1})$--.
Line 67, "$\gamma_{max}(cm^{-1})$" should read --$\nu_{max}(cm^{-1})$--.

COLUMN 32

Line 9, "µl 0" should read --µl--.
Line 27, "$\gamma_{max}(cm^{-1})$" should read --$\nu_{max}(cm^{-1})$--.
Line 52, "$\gamma_{max}(cm^{-1})$" should read --$\nu_{max}(cm^{-1})$--.

COLUMN 33

Line 14, "$\gamma_{max}(cm^{-1})$" should read --$\nu_{max}(cm^{-1})$--.
Line 33, "$\gamma_{max}(cm^{-1})$" should read --$\nu_{max}(cm^{-1})$--.
Line 55, "$^1NMR(CDCl_3)$" should read --$^1H\text{-}NMR(CDCl_3)$--.
Line 62, "$\gamma_{max}(cm^{-1})$" should read --$\nu_{max}(cm^{-1})$--.

UNITED STATES PATENT AND TRADEMARK OFFICE
CERTIFICATE OF CORRECTION

PATENT NO. : 5,084,468
DATED : January 28, 1992
INVENTOR(S) : HIROMITSU SAITO, ET AL.

It is certified that error appears in the above-identified patent and that said Letters Patent is hereby corrected as shown below:

COLUMN 34

Line 6, "mixture" should read --mixture.--.
Line 17, "$^1$NMR(CDCl$_3$-CD$_3$OD)" should read
--$^1$H-NMR(CDCl$_3$-CD$_3$OD)-- and
"(s b 1H)" should read --(s 1H)--.
Line 21, "8.5 hz)" should read --8.5 Hz)--.
Line 24, "$\gamma_{max}$(cm$^{631\ 1}$)" should read --$\nu_{max}$(cm$^{-1}$)--.
Line 25, "COMPOUND b 14" should read --COMPOUND 14--.
Line 53, "$\gamma_{max}$(cm$^{-1}$)" should read --$\nu_{max}$(cm$^{-1}$)--.

COLUMN 35

Line 2, "$\gamma_{max}$(cm$^{-1}$)" should read --$\nu_{max}$(cm$^{-1}$)--.
Line 15, "mixture" should read --mixture.--.
Line 29, "$\gamma_{max}$(cm$^{-1}$)" should read --$\nu_{max}$(cm$^{-1}$)--.
Line 41, "$\delta$8.25" should read --$\delta$(ppm); 8.25--.
Line 53, "residue" should read --residue.--.

COLUMN 36

Line 45, "1H-NMR(CDCl$_3$)" should read --$^1$H-NMR(CDCl$_3$)--.
Line 50, "288,227," should read --288, 227,--.

COLUMN 39

Line 39, "(s 3H), .56" should read --(s 3H), 1.56)--.
Line 42, "$\gamma_{max}$(cm$^{-1}$)" should read --$\nu_{max}$(cm$^{-1}$)--.
Line 60, "$\gamma_{max}$(cm$^{-1}$)" should read --$\nu_{max}$(cm$^{-1}$)--.

UNITED STATES PATENT AND TRADEMARK OFFICE
CERTIFICATE OF CORRECTION

PATENT NO. : 5,084,468
DATED : January 28, 1992
INVENTOR(S) : HIROMITSU SAITO, ET AL.

It is certified that error appears in the above-identified patent and that said Letters Patent is hereby corrected as shown below:

COLUMN 40

Line 12, "$\gamma_{max}(cm^{-1})$" should read --$\nu_{max}(cm^{-1})$--.
Line 32, "$\gamma_{max}(cm^{-1})$" should read --$\nu_{max}(cm^{-1})$--.
Line 53, "$\gamma_{max}(cm^{-1})$" should read --$\nu_{max}(cm^{-1})$--.

COLUMN 41

Line 3, "$\gamma_{max}(cm^{-1})$" should read --$\nu_{max}(cm^{-1})$--.
Line 41, "$\gamma_{max}(cm^{-1})$" should read --$\nu_{max}(cm^{-1})$--.
Line 62, "$\gamma_{max}(cm^{-1})$" should read --$\nu_{max}(cm^{-1})$--.

COLUMN 42

Line 51, "$\gamma_{max}(cm^{-1})$" should read --$\nu_{max}(cm^{-1})$--.

COLUMN 43

Line 5, "$\gamma_{max}(cm^{-1})$" should read --$\nu_{max}(cm^{-1})$--.
Line 17, "$\gamma_{max}(cm^{-1})$" should read --$\nu_{max}(cm^{-1})$--.
Line 34, "$\gamma_{max}(cm^{-1})$" should read --$\nu_{max}(cm^{-1})$--.
Line 52, "$\gamma_{max}(cm^{-1})$" should read --$\nu_{max}(cm^{-1})$--.

COLUMN 44

Line 44, "$\gamma_{max}(cm^{-1})$" should read --$\nu_{max}(cm^{-1})$--.

COLUMN 45

Line 30, "$\gamma_{max}(cm^{-1})$" should read --$\nu_{max}(cm^{-1})$--.
Line 67, "$\gamma_{max}(cm^{-1})$" should read --$\nu_{max}(cm^{-1})$--.

UNITED STATES PATENT AND TRADEMARK OFFICE
CERTIFICATE OF CORRECTION

PATENT NO. : 5,084,468
DATED : January 28, 1992
INVENTOR(S) : HIROMITSU SAITO, ET AL.

Page 5 of 5

It is certified that error appears in the above-identified patent and that said Letters Patent is hereby corrected as shown below:

COLUMN 46

Line 11, "$\gamma_{max}(cm^{-1})$" should read --$\nu_{max}(cm^{-1})$--.
Line 19, "-carboxylate" should read -- -carboxylate.--.
Line 29, "$\gamma_{max}(cm^{-1})$" should read --$\nu_{max}(cm^{-1})$--.

COLUMN 47

Line 36, "phenyl" should read --phenyl isocyanate.--.

COLUMN 49

Line 10, "$S_3$" should read --$X_3$--.
Line 27, "(d)–$R_5$–$R_6$" should read -- –$R_5$–$R_6$   (d)--.

COLUMN 50

Line 54, "represents" should read --represent--.

Signed and Sealed this

Nineteenth Day of October, 1993

Attest:

BRUCE LEHMAN

Attesting Officer

Commissioner of Patents and Trademarks